(12) United States Patent
James et al.

(10) Patent No.: US 10,610,808 B2
(45) Date of Patent: Apr. 7, 2020

(54) SUPERCRITICAL FLUID CHROMATOGRAPHY SYSTEM

(71) Applicant: Supercritical Fluid Technologies, Inc., Newark, DE (US)

(72) Inventors: Kenneth Joseph James, Newark, DE (US); Brian Jeffrey Waibel, Kennett Square, PA (US); Kenneth Richard Krewson, Allentown, NJ (US); Chinedu David Chikwem, Wilmington, DE (US); Daniel Alan Brisach, Nottingham, PA (US)

(73) Assignee: SUPERCRITICAL FLUID TECHNOLOGIES, INC., Newark, DE (US)

( * ) Notice: Subject to any disclaimer, the term of this patent is extended or adjusted under 35 U.S.C. 154(b) by 417 days.

(21) Appl. No.: 15/504,313

(22) PCT Filed: Aug. 7, 2015

(86) PCT No.: PCT/US2015/044306
§ 371 (c)(1),
(2) Date: Feb. 15, 2017

(87) PCT Pub. No.: WO2016/028521
PCT Pub. Date: Feb. 25, 2016

(65) Prior Publication Data
US 2017/0246558 A1 Aug. 31, 2017

Related U.S. Application Data

(60) Provisional application No. 62/039,083, filed on Aug. 19, 2014, provisional application No. 62/039,074, (Continued)

(51) Int. Cl.
*B01D 15/40* (2006.01)
*B04C 9/00* (2006.01)
(Continued)

(52) U.S. Cl.
CPC .......... *B01D 15/40* (2013.01); *B01D 15/165* (2013.01); *B04C 5/081* (2013.01); *B04C 5/085* (2013.01);
(Continued)

(58) Field of Classification Search
None
See application file for complete search history.

(56) References Cited

U.S. PATENT DOCUMENTS 4,187,177 A  2/1980  Stahl
4,222,414 A  9/1980  Achener
(Continued)

FOREIGN PATENT DOCUMENTS

CN  202802826  3/2013
DE  2739860 A1  3/1979

OTHER PUBLICATIONS

Campbell, et al., "Supercritical fluid fractionation of petroleum-and coal-derived mixtures" *Analytical Chemistry* 58(11):2247-2251, Sep. 1986.
(Continued)

*Primary Examiner* — Kara M Peo
(74) *Attorney, Agent, or Firm* — Devlin Law Firm LLC; James M. Lennon

(57) ABSTRACT

Provided is a supercritical fluid chromatography system, and components comprising such a system, including one or more of a supercritical fluid chiller, a supercritical fluid pressure-equalizing vessel, and a supercritical fluid cyclonic separator. The supercritical fluid chiller and the use of the chiller allow efficient and consistent pumping of liquid-phase gases employing off-the-shelf HPLC pumps in the supercritical chromatography system using liquid-phase gas mobile phase. The pressure equalizing vessel allows the use of off the shelf HPLC column cartridges in the supercritical
(Continued)

chromatography system. The cyclonic separator efficiently and effectively allows for separation of sample molecules from a liquid phase or gas phase stream of a supercritical fluid.

19 Claims, 22 Drawing Sheets

Related U.S. Application Data filed on Aug. 19, 2014, provisional application No. 62/039,066, filed on Aug. 19, 2014.

(51) Int. Cl.

| | | |
|---|---|---|
| *B04C 5/081* | (2006.01) | |
| *B04C 5/085* | (2006.01) | |
| *G01N 30/30* | (2006.01) | |
| *G01N 30/32* | (2006.01) | |
| *F25B 7/00* | (2006.01) | |
| *F25B 25/00* | (2006.01) | |
| *B01D 15/16* | (2006.01) | |
| *C07C 45/79* | (2006.01) | |
| *C07C 51/47* | (2006.01) | |
| *C07C 67/56* | (2006.01) | |
| *C07C 231/24* | (2006.01) | |
| *C09K 5/04* | (2006.01) | |
| *F25B 9/00* | (2006.01) | |
| *F25B 9/10* | (2006.01) | |
| *B01D 11/04* | (2006.01) | |
| *B01D 11/02* | (2006.01) | |
| *G01N 30/02* | (2006.01) | |

(52) U.S. Cl.
CPC ............... *B04C 9/00* (2013.01); *C07C 45/79* (2013.01); *C07C 51/47* (2013.01); *C07C 67/56* (2013.01); *C07C 231/24* (2013.01); *C09K 5/041* (2013.01); *F25B 7/00* (2013.01); *F25B 9/002* (2013.01); *F25B 9/10* (2013.01); *F25B 25/005* (2013.01); *G01N 30/30* (2013.01); *G01N 30/32* (2013.01); *B01D 11/0203* (2013.01); *B01D 11/0403* (2013.01); *B04C 2009/004* (2013.01); *G01N 2030/027* (2013.01); *Y02P 20/544* (2015.11)

(56) References Cited

U.S. PATENT DOCUMENTS

| | | |
|---|---|---|
| 4,814,089 A | 3/1989 | Kumar |
| 4,845,985 A | 7/1989 | Berger |
| 4,871,453 A | 10/1989 | Kumar |
| 5,147,538 A | 9/1992 | Wright et al. |
| 5,167,930 A | 12/1992 | Fassbender |
| 5,250,195 A | 10/1993 | Winter et al. |
| 5,384,051 A | 1/1995 | McGinness |
| 5,582,723 A | 12/1996 | Boone et al. |
| 5,601,707 A | 1/1997 | Clay et al. |
| 5,976,381 A | 11/1999 | Lundell et al. |
| 6,015,491 A | 1/2000 | Renard et al. |
| 6,086,767 A | 7/2000 | Walters et al. |
| 6,413,428 B1 | 7/2002 | Berger et al. |
| 6,561,767 B2 | 5/2003 | Berger et al. |
| 6,648,609 B2 | 11/2003 | Berger et al. |
| 6,982,007 B2 | 1/2006 | Worm et al. |
| 7,048,517 B2 | 5/2006 | Berger et al. |
| 7,083,395 B2 | 8/2006 | Maiefski et al. |
| 7,125,453 B2 | 10/2006 | D'Evelyn et al. |
| 7,937,990 B2 | 5/2011 | Nagaoka et al. |
| 8,173,024 B2 | 5/2012 | Titmas |
| 8,215,922 B2 | 7/2012 | Berger et al. |
| 8,246,834 B2 | 8/2012 | Chordia et al. |
| 8,419,936 B2 | 4/2013 | Berger et al. |
| 2002/0139752 A1 | 10/2002 | Berger et al. |
| 2005/0011835 A1 | 1/2005 | Henderson et al. |
| 2005/0247632 A1 | 11/2005 | Ellis et al. |
| 2009/0113903 A1 | 5/2009 | Babkin et al. |
| 2011/0030186 A1 | 2/2011 | Yamagata et al. |
| 2012/0122705 A1 | 5/2012 | Ting et al. |
| 2013/0015138 A1 | 1/2013 | Schlake et al. |
| 2013/0289300 A1 | 10/2013 | Yu et al. |
| 2014/0190183 A1 | 7/2014 | Berger et al. |

OTHER PUBLICATIONS

Jentoft, et al., "Apparatus for Supercritical Fluid Chromatography with Carbon Dioxide as the Mobile Phase" *Analytical Chemistry* 44(4):681-686, Apr. 1972.

Still, et al., "Rapid Chromatographic Technique for Preparative Separations with Moderate Resolution" *J. Org. Chem.* 43(14):2923-2925, 1978.

PCT International Search Report and Written Opinion of International PCT Application No. PCT/US2015/044306 dated Mar. 24, 2016, 4 pages.

European Extended Search Report of European Application No. EP15833172.8 dated Apr. 19, 2018, 8 pages.

SUPERCRITICAL FLUID CHROMATOGRAPHY SYSTEM

CROSS-REFERENCE TO RELATED APPLICATIONS

This application is the U.S. national phase under 35 U.S.C. § 371 of Intl. Appl. No. PCT/US2015/044306, filed on Aug. 7, 2015, which claims the benefit under 35 U.S.C. § 119(e) of U.S. Provisional Application No. 62/039,066, filed on Aug. 19, 2014; U.S. Provisional Application No. 62/039,074, filed on Aug. 19, 2014; and U.S. Provisional Application No. 62/039,083, filed on Aug. 19, 2014, all of which are incorporated herein by reference in their entireties for all purposes.

FIELD

Provided is a supercritical fluid chromatography system, and components comprising such a system, including one or more of a supercritical fluid chiller, a supercritical fluid pressure-equalizing vessel, and a supercritical fluid cyclonic separator.

BACKGROUND

Traditional flash chromatography is a chromatographic separation technique that is used to separate organic reaction mixtures to allow the organic chemist to crudely purify the reaction products and then use these purified products to move on to the next step of an organic synthesis. A typical pharmaceutical synthesis has many reaction steps to get from starting materials to a final product where each of these reaction products needs to be purified before moving on to the next synthetic step. The traditional flash chromatography unit employs multiple organic solvent pumps (200 psi and 200 mls/min maximum operation pressure and flow rate for a traditional flash chromatography unit), a sample injection assembly where a chemist would inject the crude reaction mix for separation, a separation column in the form of a cartridge loaded with a silica or modified silica gel, a UV-VIS detector (or other form of sample detection) to detect and allow for collection of the various fractions of the reaction mix exiting the column, and a collection tray to collect the various fractions of the reaction mixture products.

Traditional flash chromatography uses large amounts of organic solvents (for example, Hexanes, Methylene Chloride, Carbon Tetra Chloride, Acetonitrile, and Chloroform) to elucidate a separation. These solvents are typically 80-90% of the flow stream through the separation column.

In the past, we have worked on a supercritical carbon dioxide prechiller system that included a waterless refrigeration system to supply subcooling of liquefied carbon dioxide prior to flowing into a piston-style positive displacement pump.

Since this device was created, it has undergone testing with a pump meant to supply high pressure carbon dioxide (e.g. >100 bar) to a supercritical carbon dioxide (scCO2) extraction system. Despite multiple attempts to improve the mechanical behavior of the pump, the system mass flow rates were never proportionate to pump speed. This was indicative of cavitation effects in the flow system comprised of duplex pump heads, each comprised of an inlet check valve, compression piston, and outlet check valve. We made multiple attempts to characterize the system as a function of inlet pressure and temperature. Despite significant effort to characterize the behavior, the pump performance was not repeatable. Moreover, all attempts at linearization via compensation failed.

In all cases, the inlet CO2 temperature was reduced to between 2° C. and 5° C. using the waterless refrigeration system. This was readily within the range of single stage compressor.

SUMMARY

Chiller or Pre-Chiller

In one aspect, provided is a chiller. In some embodiments, the chiller comprises:
 a) a first refrigerant circuit, comprising:
  i) a first compressor that pumps refrigerant through the first refrigerant circuit;
  ii) a first tube-in-tube heat exchanger in fluid communication with the first compressor, wherein the first tube-in-tube heat exchanger comprises an inner lumen and an outer lumen that surrounds the inner lumen, wherein the refrigerant flows through the outer lumen;
 b) a cryogenic refrigerant circuit in thermodynamic communication with the first refrigerant circuit, the cryogenic refrigerant circuit comprising:
  i) a second compressor that pumps cryogenic refrigerant through the cryogenic refrigerant circuit;
  ii) the first tube-in-tube heat exchanger in fluid communication with the second compressor; wherein the cryogenic refrigerant flows through the inner lumen;
  iii) a second tube-in-tube heat exchanger in fluid communication with the first tube-in-tube heat exchanger; wherein the second tube-in-tube heat exchanger comprises an inner lumen and an outer lumen that surrounds the inner lumen, wherein the cryogenic refrigerant flows through the outer lumen and wherein liquefied gas or supercritical gas flows through the inner lumen;

wherein the chiller does not comprise an intervening medium that mediates heat exchange between the first refrigerant circuit and the cryogenic refrigerant circuit and wherein the liquefied gas or supercritical gas exiting the inner lumen of the second tube-in-tube heat exchanger is chilled. In varying embodiments, the output liquefied gas or supercritical gas is chilled at least about 35° C. lower than the input liquefied gas or supercritical gas. In varying embodiments, the refrigerant is selected from the group consisting of R-11, R-12, R-22, R-32, R-114, R-115, R-123, R-124, R-125, R-134A, R-142b, R-143a, R-152a, R-290, R-401A, R-401B, R-404A, R-407C, R 410A, R-409A, R-414B, R-416A, R-422B, R-422D, R-500, R-502, R-507, R-600 and mixtures thereof. In varying embodiments, the cryogenic refrigerant is selected from the group consisting of R-12, R-13, R-22, R-23, R-32, R-115, R 116, R-124, R-125, R-134A, R-142b, R-143a, R-152a, R-218, R-290, R-218, R-401A, R 401B, R-402A, R-402B, R-403B, R-404A, R-408A, R-409A, R-410A, R-414B, R-416A, R-422B, R-407A, R-407C, R-408A, R-409A, R-414B, R-422A, R-422B, R-422C, R-422D, R-500, R-502, R-503, R-508B, R-507, R-508B, R-600a and mixtures thereof. In varying embodiments, the first refrigerant circuit further comprises in fluid communication with the first compressor and the first tube-in-tube heat exchanger: iii) a first expansion valve; and iv) a liquid to air heat exchanger. In varying embodiments, the cryogenic refrigerant circuit further comprises in fluid communication with the second compressor, the first tube-in-tube heat exchanger and the second tubein-tube heat exchanger: iv) a second expansion valve. In varying embodiments, the chiller comprises a configuration as depicted in FIGS. 3A-3B.

In another aspect, provided are methods of supplying a liquid-phase gas to a liquefied gas or supercritical gas extraction system. In some embodiments, the methods comprise:

a) subcooling the liquid-phase gas to a temperature of −10° C. or lower;

b) pumping the subcooled liquid-phase gas into a chamber configured for extraction with liquefied gas or supercritical gas extraction, whereby the pumping mass flow rate of the subcooled liquid phase gas is repeatable and proportionate to pump speed. In varying embodiments, the subcooling is performed using a chiller as described above and herein. In varying embodiments, the liquefied gas or supercritical gas is selected from the group consisting of carbon dioxide, n-butane, n-propane, isobutane, dimethyl ether, and mixtures thereof. In varying embodiments, the liquefied gas or supercritical gas is CO2. In varying embodiments, the pumping step employs a positive displacement pump. In varying embodiments, the positive displacement pump is an unmodified high performance liquid chromatography (HPLC) pump. In varying embodiments, the system further comprises a post-pump heater downstream of and in fluid communication with the pump, wherein the post-pump heater heats the liquefied gas or supercritical gas up to an operational temperature. In varying embodiments, the liquefied carbon dioxide is subcooled to a temperature in the range of about −10° C. to about −40° C. In varying embodiments, the liquefied carbon dioxide is subcooled to a temperature in the range of about −20° C. to about −40° C. In varying embodiments, the subcooling of the liquified gas is performed employing a 2-stage refrigerant-on-refrigerant chiller system. In varying embodiments, the pumping step employs a pump comprising at least one pump head and the method does not comprise separately cooling the at least one pump head. In varying embodiments, the liquefied gas or supercritical gas is pressurized to at least about 145 psi (at least about 10 bar).

In a further aspect, provided is a system comprising a chiller as described above and herein. In some embodiments, the system comprises:

a) a tank comprising a gas stored at saturated conditions and a liquid withdrawal means;

b) a chiller downstream of and in fluid communication with the tank, wherein the chiller subcools the gas to a temperature of −10° C. or lower;

c) a pump downstream of and in fluid communication with the tank and the chiller and a chamber configured for liquefied gas or supercritical gas extraction, wherein the pump comprises the gas at a temperature of −10° C. or lower; wherein the mass flow rate of the subcooled liquid phase gas through the pump is repeatable and proportionate to pump speed. In some embodiments, the gas is selected from the group consisting of carbon dioxide, n-butane, n-propane, isobutane, dimethyl ether, and mixtures thereof. In some embodiments, the pump is a positive displacement pump. In some embodiments, the positive displacement pump is an unmodified high performance liquid chromatography (HPLC) pump.

In various embodiments, the system further comprises a cyclonic separator comprising:

a) a cyclone body comprising an inner surface, an outer circumference, a top outlet, a tangential inlet and a bottom outlet, wherein the inner surface comprises a top portion, a middle portion and a bottom portion, wherein:

i) the top portion of the inner surface comprises screw threads;
ii) the middle portion of the inner surface is cylindrical;
iii) the bottom portion of the inner surface comprises a funnel, wherein the funnel has an angle in the range of about 30° to about 60°; and wherein the ratio of the diameter of the outer circumference to the inner diameter of the mid-height of the funnel is in the range of about 3 to about 4; and b) a cap comprising a scintered filter and screw threads, wherein the screw threads of the cap interlock with the screw threads on the inner surface of the top portion of the cyclone body, wherein the cyclonic separator can withstand pressures of at least about 1000 psi, and wherein the body is in fluid communication with the cap. In varying embodiments, the bottom outlet of the body of the cyclonic separator is attached to a collection container, wherein the body is in fluid communication with the collection container. In varying embodiments, the cyclonic separator can withstand pressures of up to about 2000 psi. In varying embodiments, the cyclonic separator can withstand pressures of up to about 1500 psi. In varying embodiments, the thickness of the middle portion and the bottom portion of the cyclone body is at least about 0.30 inches. In varying embodiments, the cyclone body is made of a material selected from the group consisting of: stainless steel and titanium. In varying embodiments, the stainless steel comprises an austenitic nickel-chromium-based alloy or a martensitic nickel-chromium-based alloy. In varying embodiments, the stainless steel comprises less than about 0.1 wt. % carbon. In varying embodiments, the stainless steel comprises at least a 30,000 psi yield strength. In varying embodiments, the stainless steel is selected from the group consisting of American Iron and Steel Institute (AISI) TYPE 304 SS, AISI TYPE 316L, INCONEL® alloy 625, INCONEL® alloy 718, AK Steel 17-4 PH®, HASTELLOY® C-22 and HASTELLOY® C 276. In varying embodiments, the stainless steel is a nickel-chromium superalloy selected from the group consisting of INCONEL® alloy 625, INCONEL® alloy 718, AK Steel 17-4 PH®, HASTELLOY® C-22 and HASTELLOY® C 276. In varying embodiments, the inner surface of the cyclone body is configured to induce or guide a conical cyclone of fluid flowing in from the tangential inlet. In varying embodiments, the inner surface of the cyclone body does not comprise a filter or a porous surface. In varying embodiments, the inner surface of the cyclone body does not comprise one or more baffles. In varying embodiments, the cyclone body does not comprise multiple inlets. In varying embodiments, the sintered filter within the cap comprises a G-5 porosity grade (1-16 microns pore size). In varying embodiments, the funnel has an angle of about 40°; and wherein the ratio of the diameter of the outer circumference to the inner diameter of the mid-height of the funnel is about 3.5. In varying embodiments, the bottom outlet remains open. In varying embodiments, the cyclonic separator is as depicted in any one of FIGS. 13 to 17. In varying embodiments, the system comprises 2 to 8 cyclonic separators, e.g., 2, 3, 4, 5, 6, 7 or 8 cyclonic separators. In varying embodiments, the interior of the cyclonic separator is in fluid connection with atmospheric pressure.

In varying embodiments, the system further comprises a pressure equalizing vessel downstream of and in fluid communication with the chiller and the pump and upstream of and in fluid communication with the cyclonic separator, the pressure equalizing vessel comprising:

i) an inner chromatography column comprising stationary phase media; and ii) an outer column that cylindrically surrounds the length of the inner column, wherein the interspace between the inner diameter of the outer column and the outer diameter of the inner chromatography column comprises a width of at least 1 mm, wherein the outer column withstands pressures of at least about 500 psi (about 35 bar), and wherein no part of the inner column is exposed to full internal pressure without balancing external equalizing pressure. In varying embodiments, the interspace between the inner diameter of the outer column and the outer diameter of the inner chromatography column is filled with a supercritical fluid. In varying embodiments, the inner column and the outer column can be concurrently filled with supercritical fluid under a pressure in the range of about 500 psi (about 35 bar) to about 20,000 psi (about 1380 bar). In varying embodiments, the inner column and the outer column can be concurrently filled with supercritical fluid under a pressure in the range of at least about 5076 psi (at least about 350 bar). In varying embodiments, the pressure differential across the inner column from top to bottom is less than the pressure rating of the inner column. In varying embodiments, the pressure differential between the internal space of the inner column and the interspace is at or less than about 200 psi (about 14 bar). In varying embodiments, the pressure within the interspace is higher than the pressure within the internal space of the inner column. In varying embodiments, the inner column comprises an inlet end and an outlet end and the pressure at the inlet end is substantially the same as the pressure at the outlet end. In varying embodiments, the inner column is an off-the-shelf column compatible for use in a flash chromatography system. In varying embodiments, the inner column comprises a size in the range of from about 4 grams to about 350 grams stationary phase media. In varying embodiments, the inner column comprises a diameter in the range of about 0.5 inches to about 3.5 inches and a column length in the range from about 3.5 inches to about 11 inches. In varying embodiments, the stationary phase comprises an average particle size in the range of about 10 to about 100 microns. In varying embodiments, the vessel comprises an inlet adaptor which fits to a female slip or luer-lock connector. In varying embodiments, the vessel comprises an outlet adaptor which fits to a male slip or luer-lock connector. In varying embodiments, the outlet adaptor comprises an O ring that seals around the male slip or luer-lock connector. In varying embodiments, the inner column comprises an inlet end and an outlet end, wherein neither the inlet end nor the outlet end of the inner column comprises a perforated stopper. In varying embodiments, the interspace comprises a single inlet and no outlet or vent. In varying embodiments, the pressure equalizing column is as depicted in FIGS. 11 and 12.

In varying embodiments, the liquefied gas or supercritical gas is CO2. In varying embodiments, the liquefied gas or supercritical gas is pressurized to at least about 145 psi (10 bar). In varying embodiments, the flow of the supercritical solvent through the system is in the range of about 10 ml/min, e.g., at least about 15 ml/min, 20 ml/min, 25 ml/min, 30 ml/min, 35 ml/min, 40 ml/min, 45 ml/min, or 50 ml/min, to about 300 ml/min. In varying embodiments, the system further pumps a co-solvent. In some embodiments, the co-solvent comprises an alcohol of 3 or fewer carbon atoms (e.g., methanol, ethanol, propanol, isopropanol) or an acetate of 3 or fewer carbon atoms (e.g., methyl acetate, ethyl acetate, propyl acetate), or mixtures thereof. In varying embodiments, the system is as depicted in FIG. 1.

In another aspect, provided are methods of performing high pressure separation and/or extraction procedures using a flash chromatography system. In some embodiments, the methods comprise inputting a stream of gas phase supercritical fluid comprising molecules into a chiller as described above and herein.

Pressure Equalizing Vessel

In one aspect, provided is a pressure equalizing chromatography vessel comprising:

i) an inner chromatography column comprising stationary phase media; and ii) an outer column that cylindrically surrounds the length of the inner column, wherein the interspace between the inner diameter of the outer column and the outer diameter of the inner chromatography column comprises a width of at least 1 mm, wherein the outer column withstands pressures of at least about 500 psi (about 35 bar), and wherein no part of the inner column is exposed to full internal pressure without balancing external equalizing pressure. In varying embodiments, the interspace between the inner diameter of the outer column and the outer diameter of the inner chromatography column is filled with a supercritical fluid. In varying embodiments, the inner column and the outer column can be concurrently filled with supercritical fluid under a pressure in the range of about 500 psi (about 35 bar) to about 20,000 psi (about 1380 bar). In varying embodiments, the inner column and the outer column can be concurrently filled with supercritical fluid under a pressure of at least about 5076 psi (at least about 350 bar). In varying embodiments, the pressure differential across the inner column from top to bottom is less than the pressure rating for the inner column. In varying embodiments, the pressure differential between the internal space of the inner column and the interspace is at or less than about 200 psi (about 14 bar). In varying embodiments, the pressure within the interspace is higher than the pressure within the internal space of the inner column. In varying embodiments, the inner column comprises an inlet end and an outlet end and the pressure at the inlet end is substantially the same as the pressure at the outlet end. In varying embodiments, the inner column is an off-the-shelf column compatible for use in a flash chromatography system. In varying embodiments, the inner column comprises a size in the range of from about 4 grams to about 350 grams stationary phase media. In varying embodiments, the inner column comprises a diameter in the range of about 0.5 inches to about 3.5 inches and a column length in the range from about 3.5 inches to about 11 inches. In varying embodiments, the stationary phase comprises an average particle size in the range of about 10 to about 100 microns. In varying embodiments, the vessel comprises an inlet adaptor which fits to a female slip or luer-lock connector. In varying embodiments, the vessel comprises an outlet adaptor which fits to a male slip or luer-lock connector. In varying embodiments, the outlet adaptor comprises an O-ring that seals around the male slip or luer-lock connector. In varying embodiments, the inner column comprises an inlet end and an outlet end, wherein neither the inlet end nor the outlet end of the inner column comprises a perforated stopper. In varying embodiments, the interspace comprises a single inlet and no outlet or vent. In varying embodiments, the pressure equalizing column is as depicted in FIGS. 11 and 12.

In another aspect, provided is a chromatography system comprising the pressure equalizing vessel as described above and herein, wherein the system is pressurized and pumps a supercritical solvent. In some embodiments, the system further comprises a supercritical solvent pump upstream of and in fluid communication with the pressure equalizing vessel and a chiller upstream of and in fluid communication with the pump, wherein the chiller reduces the temperature of the supercritical solvent to about −5° C. or lower, e.g., about −10° C., −15° C., −20° C., −25° C., or lower. In some embodiments, the chiller comprises:

a) a first refrigerant circuit, comprising:
  i) a first compressor that pumps refrigerant through the first refrigerant circuit;
  ii) a first tube-in-tube heat exchanger in fluid communication with the first compressor, wherein the first tube-in-tube heat exchanger comprises an inner lumen and an outer lumen that surrounds the inner lumen, wherein the refrigerant flows through the outer lumen;
b) a cryogenic refrigerant circuit in thermodynamic communication with the first refrigerant circuit, the cryogenic refrigerant circuit comprising:
  i) a second compressor that pumps cryogenic refrigerant through the cryogenic refrigerant circuit;
  ii) the first tube-in-tube heat exchanger in fluid communication with the second compressor; wherein the cryogenic refrigerant flows through the inner lumen;
  iii) a second tube-in-tube heat exchanger in fluid communication with the first tube-in-tube heat exchanger; wherein the second tube-in-tube heat exchanger comprises an inner lumen and an outer lumen that surrounds the inner lumen, wherein the cryogenic refrigerant flows through the outer lumen and wherein liquefied gas or supercritical gas flows through the inner lumen;
wherein the chiller does not comprise an intervening medium that mediates heat exchange between the first refrigerant circuit and the cryogenic refrigerant circuit and wherein the liquefied gas or supercritical gas exiting the inner lumen of the second tube-in-tube heat exchanger is chilled. In varying embodiments, the output liquefied gas or supercritical gas is chilled at least about 35° C. lower than the input liquefied gas or supercritical gas. In varying embodiments, the refrigerant is selected from the group consisting of R-11, R-12, R-22, R-32, R-114, R-115, R-123, R-124, R-125, R-134A, R-142b, R-143a, R-152a, R-290, R-401A, R-401B, R-404A, R-407C, R 410A, R-409A, R-414B, R-416A, R-422B, R-422D, R-500, R-502, R-507, R-600 and mixtures thereof. In varying embodiments, the cryogenic refrigerant is selected from the group consisting of R-12, R-13, R-22, R-23, R-32, R-115, R 116, R-124, R-125, R-134A, R-142b, R-143a, R-152a, R-218, R-290, R-218, R-401A, R 401B, R-402A, R-402B, R-403B, R-404A, R-408A, R-409A, R-410A, R-414B, R-416A, R-422B, R-407A, R-407C, R-408A, R-409A, R-414B, R-422A, R-422B, R-422C, R-422D, R-500, R-502, R-503, R-508B, R-507, R-508B, R-600a and mixtures thereof. In varying embodiments, the first refrigerant circuit further comprises in fluid communication with the first compressor and the first tube-in-tube heat exchanger: iii) a first expansion valve; and iv) a liquid to air heat exchanger. In varying embodiments, the cryogenic refrigerant circuit further comprises in fluid communication with the second compressor, the first tube-in-tube heat exchanger and the second tube-in-tube heat exchanger: iv) a second expansion valve. In varying embodiments, the chiller comprises a configuration as depicted in FIGS. 3A-3B. In some embodiments, the system comprises:

a) a tank comprising a gas stored at saturated conditions and a liquid withdrawal means;
b) a chiller in fluid communication with the tank, wherein the chiller subcools the gas to a temperature of −10° C. or lower;
c) a pump in fluid communication with the tank and a chamber configured for liquefied gas or supercritical gas extraction, wherein the pump comprises the gas at a temperature of −10° C. or lower; wherein the mass flow rate of the subcooled liquid phase gas through the pump is repeatable and proportionate to pump speed. In some embodiments, the gas is selected from the group consisting of carbon dioxide, n-butane, n-propane, isobutane, dimethyl ether, and mixtures thereof. In some embodiments, the pump is a positive displacement pump. In some embodiments, the positive displacement pump is an unmodified high performance liquid chromatography (HPLC) pump. In varying embodiments, the system further comprises a post-pump heater downstream of and in fluid communication with the pump, wherein the post-pump heater heats the liquefied gas or supercritical gas up to an operational temperature.

In varying embodiments, the supercritical fluid is CO2. In varying embodiments, the flow of the supercritical solvent through the system is in the range of about 10 ml/min, e.g., at least about 15 ml/min, 20 ml/min, 25 ml/min, 30 ml/min, 35 ml/min, 40 ml/min, 45 ml/min, or 50 ml/min, to about 300 ml/min. In varying embodiments, the system further pumps a co-solvent. In some embodiments, the co-solvent comprises an alcohol of 3 or fewer carbon atoms (e.g., methanol, ethanol, propanol, isopropanol) or an acetate of 3 or fewer carbon atoms (e.g., methyl acetate, ethyl acetate, propyl acetate), or mixtures thereof. In varying embodiments, the system is as depicted in FIG. 1.

In varying embodiments, the system further comprises a cyclonic separator downstream of and in fluid communication with the pressure equalizing vessel, the cyclonic separator comprising:

a) a cyclone body comprising an inner surface, an outer circumference, a top outlet, a tangential inlet and a bottom outlet, wherein the inner surface comprises a top portion, a middle portion and a bottom portion, wherein:
  i) the top portion of the inner surface comprises screw threads;
  ii) the middle portion of the inner surface is cylindrical;
  iii) the bottom portion of the inner surface comprises a funnel, wherein the funnel has an angle in the range of about 30° to about 60°; and wherein the ratio of the diameter of the outer circumference to the inner diameter of the mid-height of the funnel is in the range of about 3 to about 4; and
b) a cap comprising a sintered filter and screw threads, wherein the screw threads of the cap interlock with the screw threads on the inner surface of the top portion of the cyclone body, wherein the cyclonic separator can withstand pressures of at least about 1000 psi, and wherein the body is in fluid communication with the cap. In varying embodiments, the bottom outlet of the body is attached to a collection container, wherein the body is in fluid communication with the collection container. In some embodiments, the cyclonic separator can withstand pressures of up to about 10,000 psi, e.g, up to about 5000 psi, e.g., up to about 2000 psi, e.g., up to about 1900 psi, 1800 psi, 1700 psi, 1600 psi, or 1500 psi. In varying embodiments, the thickness of the middle portion and the bottom portion of the cyclone body is at least about 0.30 inches, e.g., at least about 0.31, 0.32, 0.33, 0.34, 0.35, 0.36, 0.37, 0.375, 0.38, 0.39, 0.40 inches. In varying embodiments, the cyclone body is made of a material selected from the group consisting of: stainless steel and titanium. In varying embodiments, the stainless steel comprises an austenitic nickel-chromium-based alloy or a martensitic nickel-chromium-based alloy. In varying embodiments, the stainless steel comprises less than about 0.1 wt. % carbon. In varying embodiments, the stainless steel comprises at least a 30,000 psi yield strength. In varying embodiments, the stainless steel is selected from the group consisting of American Iron and Steel Institute (AISI) TYPE 304 SS, AISI TYPE 316L, INCONEL® alloy 625, INCONEL® alloy 718, AK Steel 17-4 PH®, HASTELLOY® C-22 and HASTELLOY® C-276. In varying embodiments, the stainless steel is a nickel-chromium superalloy selected from the group consisting of INCONEL® alloy 625, INCONEL® alloy 718, HASTELLOY® C-22 and HASTELLOY® C-276. In some embodiments, the inner surface of the cyclone body is configured to induce or guide a conical cyclone of fluid flowing in from the tangential inlet. In varying embodiments, the inner surface of the cyclone body does not comprise a filter or a porous surface. In varying embodiments, the inner surface of the cyclone body does not comprise one or more baffles. In some embodiments, the cyclone body does not comprise multiple inlets. In some embodiments, the sintered filter within the cap comprises a G-5 porosity grade (1-16 microns pore size). In some embodiments, the funnel has an angle of about 40'; and the ratio of the diameter of the outer circumference to the inner diameter of the mid-height of the funnel is about 3.5. In varying embodiments, the bottom outlet remains open. In some embodiments, the cyclonic separator is as depicted in any one of FIGS. 13 to 17.

In a further aspect, provided is a chromatography system comprising one or more cyclonic separators as described above and herein, wherein the chromatography system is pressurized and pumps a supercritical solvent. In varying embodiments, the system comprises 2 to 8 cyclonic separators, e.g., 2, 3, 4, 5, 6, 7 or 8 cyclonic separators. In varying embodiments, the interior of the cyclonic separator is in fluid connection with atmospheric pressure.

In another aspect, provided are methods of performing high pressure separation and/or extraction procedures using a flash chromatography system, comprising separating sample in a supercritical fluid mobile phase in the inner chromatography column of the pressure equalizing vessel as described above and herein.

Cyclonic Separator

In one aspect, provided is a cyclonic separator comprising:

a) a cyclone body comprising an inner surface, an outer circumference, a top outlet, a tangential inlet and a bottom outlet, wherein the inner surface comprises a top portion, a middle portion and a bottom portion, wherein:

i) the top portion of the inner surface comprises screw threads;

ii) the middle portion of the inner surface is cylindrical;

iii) the bottom portion of the inner surface comprises a funnel, wherein the funnel has an angle in the range of about 30° to about 60°; and wherein the ratio of the diameter of the outer circumference to the inner diameter of the mid-height of the funnel is in the range of about 3 to about 4; and b) a cap comprising a sintered filter and screw threads, wherein the screw threads of the cap interlock with the screw threads on the inner surface of the top portion of the cyclone body, wherein the cyclonic separator can withstand pressures of at least about 1000 psi, and wherein the body is in fluid communication with the cap. In varying embodiments, the bottom outlet of the body is attached to a collection container, wherein the body is in fluid communication with the collection container. In some embodiments, the cyclonic separator can withstand pressures of up to about 10,000 psi, e.g, up to about 5000 psi, e.g., up to about 2000 psi, e.g., up to about 1900 psi, 1800 psi, 1700 psi, 1600 psi, or 1500 psi. In varying embodiments, the thickness of the middle portion and the bottom portion of the cyclone body is at least about 0.30 inches, e.g., at least about 0.31, 0.32, 0.33, 0.34, 0.35, 0.36, 0.37, 0.375, 0.38, 0.39, 0.40 inches. In varying embodiments, the cyclone body is made of a material selected from the group consisting of: stainless steel and titanium. In varying embodiments, the stainless steel comprises an austenitic nickel-chromium-based alloy or a martensitic nickel-chromium-based alloy. In varying embodiments, the stainless steel comprises less than about 0.1 wt. % carbon. In varying embodiments, the stainless steel comprises at least a 30,000 psi yield strength. In varying embodiments, the stainless steel is selected from the group consisting of American Iron and Steel Institute (AISI) TYPE 304 SS, AISI TYPE 316L, INCONEL® alloy 625, INCONEL® alloy 718, AK Steel 17-4 PH®, HASTELLOY® C-22 and HASTELLOY® C-276. In varying embodiments, the stainless steel is a nickel-chromium superalloy selected from the group consisting of INCONEL® alloy 625, INCONEL® alloy 718, HASTELLOY® C-22 and HASTELLOY® C-276. In some embodiments, the inner surface of the cyclone body is configured to induce or guide a conical cyclone of fluid flowing in from the tangential inlet. In varying embodiments, the inner surface of the cyclone body does not comprise a filter or a porous surface. In varying embodiments, the inner surface of the cyclone body does not comprise one or more baffles. In some embodiments, the cyclone body does not comprise multiple inlets. In some embodiments, the sintered filter within the cap comprises a G-5 porosity grade (1-16 microns pore size). In some embodiments, the funnel has an angle of about 40°; and the ratio of the diameter of the outer circumference to the inner diameter of the mid-height of the funnel is about 3.5. In varying embodiments, the bottom outlet remains open. In some embodiments, the cyclonic separator is as depicted in any one of FIGS. 13 to 17.

In a further aspect, provided is a chromatography system comprising one or more cyclonic separators as described above and herein, wherein the chromatography system is pressurized and pumps a supercritical solvent. In varying embodiments, the system comprises 2 to 8 cyclonic separators, e.g., 2, 3, 4, 5, 6, 7 or 8 cyclonic separators. In varying embodiments, the interior of the cyclonic separator is in fluid connection with atmospheric pressure.

In varying embodiments, the chromatography system further comprises a pressure equalizing vessel upstream of and in fluid communication with the cyclonic separator, the pressure equalizing vessel comprising:

i) an inner chromatography column comprising stationary phase media; and ii) an outer column that cylindrically surrounds the length of the inner column, wherein the interspace between the inner diameter of the outer column and the outer diameter of the inner chromatography column comprises a width of at least 1 mm, wherein the outer column withstands pressures of at least about 500 psi (about 35 bar), and wherein no part of the inner column is exposed to full internal pressure without balancing external equalizing pressure. In varying embodiments, the interspace has a width of up to about 2, 3, 4, 5, 6, 7, 8, 9, 10, 11, 12, 13, 14, 15, 16, 17, 18, 19 or 20 mm. In varying embodiments of the pressure equalizing vessel, the interspace between the inner diameter of the outer column and the outer diameter of the inner chromatography column is filled with a supercritical fluid. In some embodiments, the inner column and the outer column can be concurrently filled with supercritical fluid under a pressure in the range of about 500 psi (about 35 bar) to about 20,000 psi (about 1380 bar). In some embodiments, the inner column and the outer column can be concurrently filled with supercritical fluid under a pressure in the range of at least about 5076 psi (at least about 350 bar). In some embodiments, the pressure differential across the inner column from top to bottom is less than the pressure rating of the inner column. Generally, the pressure differential between the internal space of the inner column and the interspace is less than the pressure rating of the inner column. In some embodiments, the pressure differential between the internal space of the inner column and the interspace is at or less than about 200 psi (about 14 bar). In some embodiments, the pressure within the interspace is higher than the pressure within the internal space of the inner column. In some embodiments, the inner column comprises an inlet end and an outlet end and the pressure at the inlet end is substantially the same as the pressure at the outlet end. In some embodiments, the inner column is an off-the-shelf column compatible for use in a flash chromatography system. In some embodiments, the inner column comprises a size in the range of from about 4 grams to about 350 grams stationary phase media. In some embodiments, the inner column comprises a diameter in the range of about 0.5 inches to about 3.5 inches and a column length in the range from about 3.5 inches to about 11 inches. In some embodiments, the stationary phase comprises an average particle size in the range of about 10 to about 100 microns, e.g., in the range of about 20 to about 80 microns. In some embodiments, the pressure equalizing vessel comprises an inlet adaptor which fits to a female slip or luer-lock connector. In some embodiments, the pressure equalizing vessel comprises an outlet adaptor which fits to a male slip or luer-lock connector. In some embodiments, the outlet adaptor comprises an 0-ring that seals around the male slip or luer-lock connector. In some embodiments, the inner column comprises an inlet end and an outlet end, wherein neither the inlet end nor the outlet end of the inner column comprises a perforated stopper. In some embodiments, the interspace comprises a single inlet and no outlet or vent. In some embodiments, the pressure equalizing column is as depicted in FIGS. 11 and 12.

In varying embodiments, the chromatography system further comprises a supercritical solvent pump and a chiller in fluid communication with and upstream of the pump and the cyclonic separator, wherein the chiller reduces the temperature of the supercritical solvent to about −5° C. or lower, e.g., about −10° C., −15° C., −20° C., −25° C., or lower. In some embodiments, the chiller comprises:
  a) a first refrigerant circuit, comprising:
  i) a first compressor that pumps refrigerant through the first refrigerant circuit;
  ii) a first tube-in-tube heat exchanger in fluid communication with the first compressor, wherein the first tube-in-tube heat exchanger comprises an inner lumen and an outer lumen that surrounds the inner lumen, wherein the refrigerant flows through the outer lumen;
  b) a cryogenic refrigerant circuit in thermodynamic communication with the first refrigerant circuit, the cryogenic refrigerant circuit comprising:
  i) a second compressor that pumps cryogenic refrigerant through the cryogenic refrigerant circuit;
  ii) the first tube-in-tube heat exchanger in fluid communication with the second compressor; wherein the cryogenic refrigerant flows through the inner lumen;
  iii) a second tube-in-tube heat exchanger in fluid communication with the first tube-in-tube heat exchanger; wherein the second tube-in-tube heat exchanger comprises an inner lumen and an outer lumen that surrounds the inner lumen, wherein the cryogenic refrigerant flows through the outer lumen and wherein liquefied gas or supercritical gas flows through the inner lumen;

wherein the chiller does not comprise an intervening medium that mediates heat exchange between the first refrigerant circuit and the cryogenic refrigerant circuit and wherein the liquefied gas or supercritical gas exiting the inner lumen of the second tube-in-tube heat exchanger is chilled. In varying embodiments, the output liquefied gas or supercritical gas is chilled at least about 35° C. lower than the input liquefied gas or supercritical gas. In varying embodiments, the refrigerant is selected from the group consisting of R-11, R-12, R-22, R-32, R-114, R-115, R-123, R-124, R-125, R-134A, R-142b, R-143a, R-152a, R-290, R-401A, R-401B, R-404A, R-407C, R 410A, R-409A, R-414B, R-416A, R-422B, R-422D, R-500, R-502, R-507, R-600 and mixtures thereof. In varying embodiments, the cryogenic refrigerant is selected from the group consisting of R-12, R-13, R-22, R-23, R-32, R-115, R 116, R-124, R-125, R-134A, R-142b, R-143a, R-152a, R-218, R-290, R-218, R-401A, R 401B, R-402A, R-402B, R-403B, R-404A, R-408A, R-409A, R-410A, R-414B, R-416A, R-422B, R-407A, R-407C, R-408A, R-409A, R-414B, R-422A, R-422B, R-422C, R-422D, R-500, R-502, R-503, R-508B, R-507, R-508B, R-600a and mixtures thereof. In varying embodiments, the first refrigerant circuit further comprises in fluid communication with the first compressor and the first tube-in-tube heat exchanger: iii) a first expansion valve; and iv) a liquid to air heat exchanger. In varying embodiments, the cryogenic refrigerant circuit further comprises in fluid communication with the second compressor, the first tube-in-tube heat exchanger and the second tube-in-tube heat exchanger: iv) a second expansion valve. In varying embodiments, the chiller comprises a configuration as depicted in FIGS. 3A-3B. In some embodiments, the system comprises:
  a) a tank comprising a gas stored at saturated conditions and a liquid withdrawal means;
  b) a chiller in fluid communication with the tank, wherein the chiller subcools the gas to a temperature of −10° C. or lower;
  c) a pump downstream of and in fluid communication with the tank and the chiller, and a chamber configured for liquefied gas or supercritical gas extraction, wherein the pump comprises the gas at a temperature of −10° C. or lower; wherein the mass flow rate of the subcooled liquid phase gas through the pump is repeatable and proportionate to pump speed. In some embodiments, the gas is selected from the group consisting of carbon dioxide, n-butane, n-propane, isobutane, dimethyl ether, and mixtures thereof. In some embodiments, the pump is a positive displacement pump. In some embodiments, the positive displacement pump is an unmodified high performance liquid chromatography (HPLC) pump. In varying embodiments, the system further comprises a post-pump heater downstream of and in fluid communication with the pump, wherein the post-pump heater heats the liquefied gas or supercritical gas up to an operational temperature.

In varying embodiments, the supercritical fluid is CO2. In varying embodiments, the flow of the supercritical solvent through the system is in the range of about 10 ml/min, e.g., at least about 15 ml/min, 20 ml/min, 25 ml/min, 30 ml/min, 35 ml/min, 40 ml/min, 45 ml/min, or 50 ml/min, to about 300 ml/min. In varying embodiments, the system further pumps a co-solvent. In some embodiments, the co-solvent comprises an alcohol of 3 or fewer carbon atoms (e.g., methanol, ethanol, propanol, isopropanol) or an acetate of 3 or fewer carbon atoms (e.g., methyl acetate, ethyl acetate, propyl acetate), or mixtures thereof. In varying embodiments, the system is as depicted in FIG. 1.

In a related aspect, provided are methods of separating molecules from a supercritical fluid. In varying embodiments, the methods comprise inputting a stream of gas phase supercritical fluid comprising molecules into the tangential inlet of a cyclonic separator as described above and herein, wherein the stream of supercritical fluid rotates around the inner surface of the cyclone body, wherein the molecules separate from the stream, slide down the inner surface and exit the cyclone body into the collection container; and wherein the gas phase supercritical fluid exits through the cap, and wherein any molecules still in the fluid stream do not escape through the sintered filter of the cap. In varying embodiments, the interior of the cyclonic separator is in fluid connection with atmospheric pressure.

Definitions

The phrase "conical cyclone of fluid" refers to a downward spiral path which substantially does not cross itself.

BRIEF DESCRIPTION OF THE DRAWINGS

FIG. 3A illustrates a block diagram of the chiller's two circuit cascade refrigeration system. FIG. 3B illustrates the chiller and HPLC pumps package. The post pump heater is used to bring process fluids up to operational temperatures.

DETAILED DESCRIPTION

1. Introduction

Provided are supercritical fluid chromatography systems that enable the separation cartridges employed in traditional flash chromatography applications to be used in conjunction with a liquefied gas or supercritical fluid dominated solvent system. This facilitates or allows for a substantial reduction on the order 80-90% of the organic solvents or a complete elimination of organic solvents in the separation process. Achieving this goal involves implementation of one or more features to enable operating conditions in the range of pressures associated with subcritical fluids or subcritical fluids, e.g., in a pressure range of about 35 bar or higher pressure. These features include a prechiller system, a pressure equalizing vessel, and a pressurized cyclonic separator. When used in coordination, these improvements allow for liquefied gas and supercritical fluids to be utilized where only low pressure liquid solvents could previously been employed. The prechiller system enables a standard HPLC pump, nominally optimized for operation with incompressible fluids, to be employed with a liquefied gas or supercritical fluid. The pressure equalizing vessel enables an off-the-shelf chromatography cartridge, nominally intended for use with low pressure liquid solvents, to be used without further alteration in a liquefied gas or supercritical fluid system. The high pressure cyclonic separator enables product recovery from a high pressure system and serves the purpose of a collection flask in a high pressure system.

2. Supercritical Fluid Chromatography Systems

Figure 1:
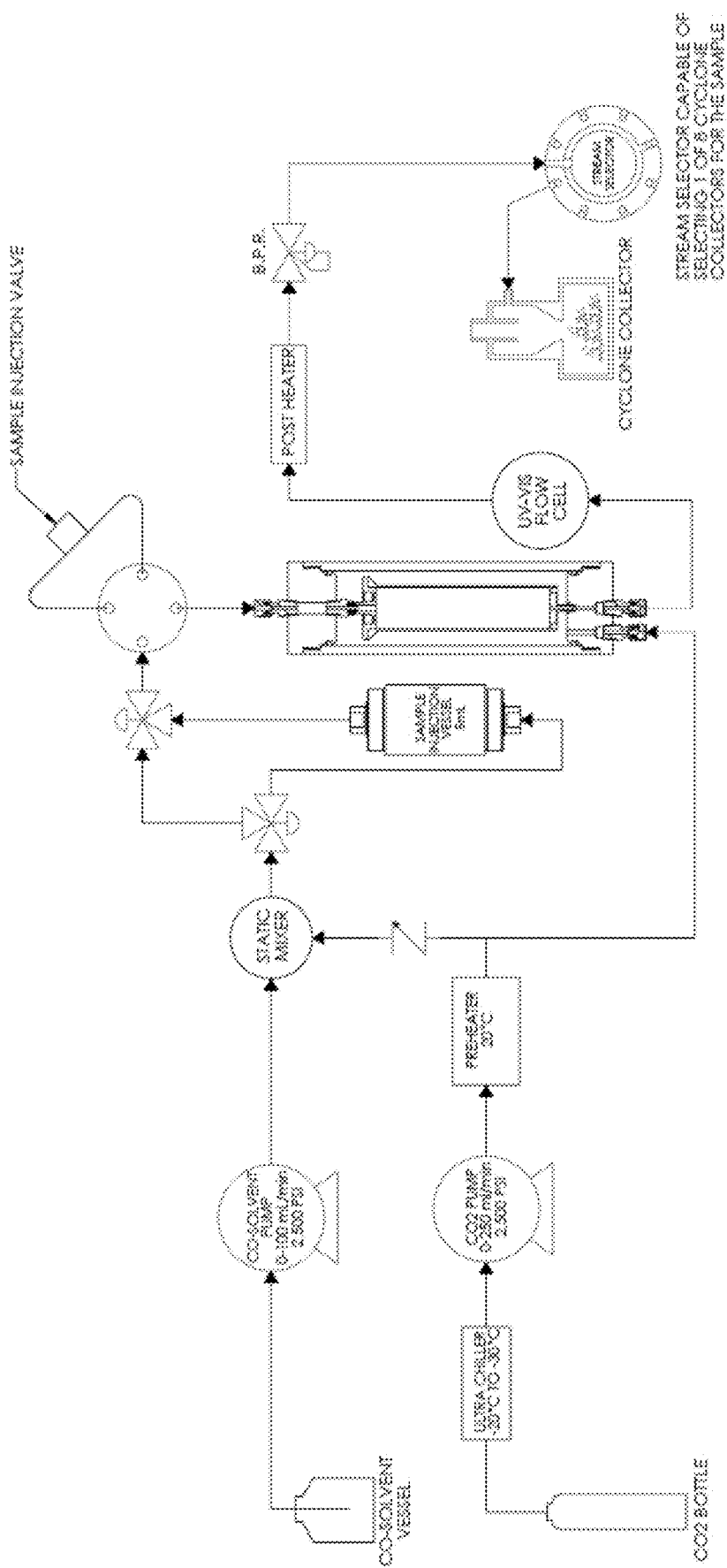
FIG. 1 illustrates a flow schematic of a chromatography system described herein.
Figure 2:
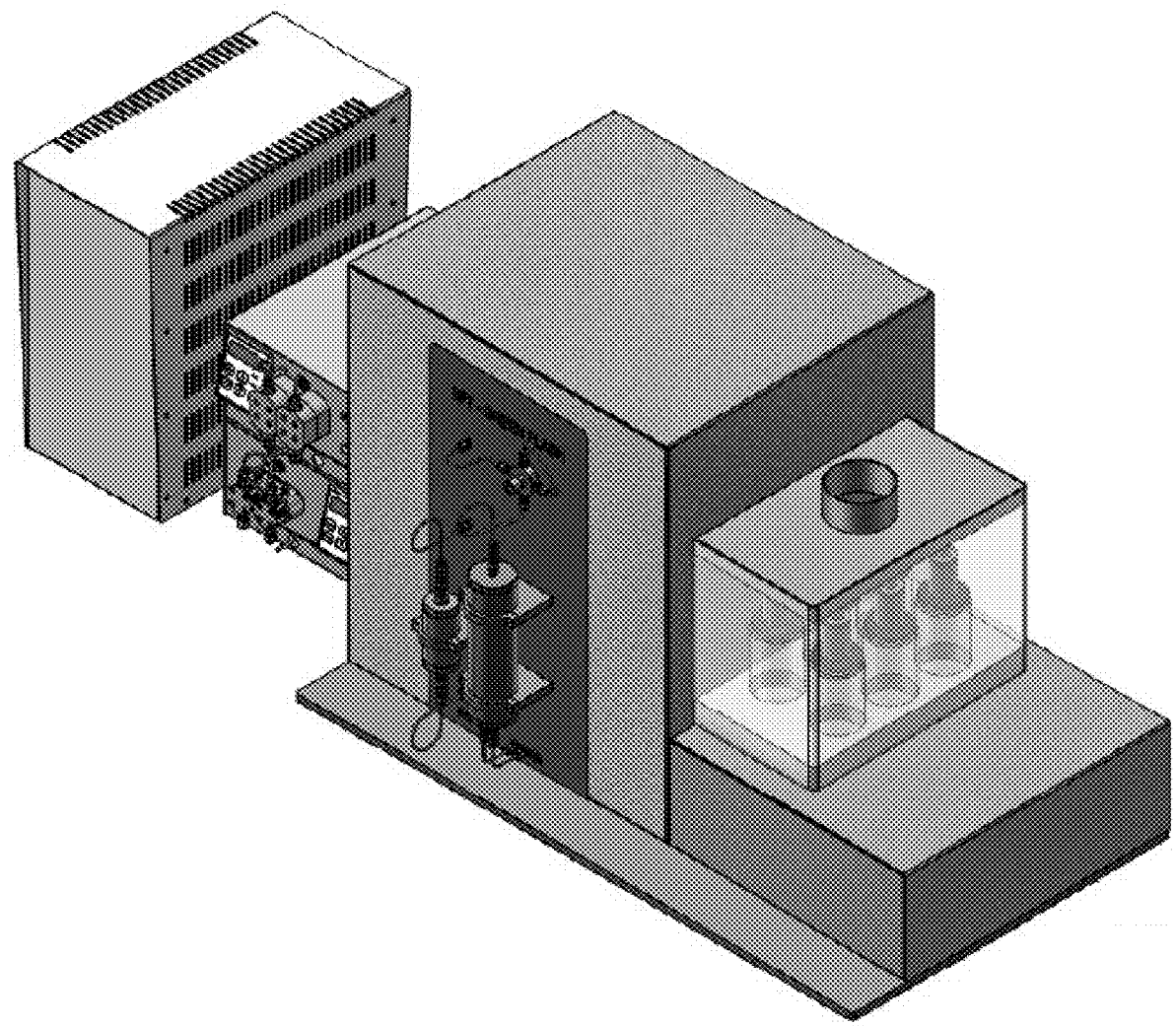
FIG. 2 illustrates an apparatus schematic of a chromatography system described herein.

The chromatography systems described herein are based, in part, on the discovery and advanced design of traditional flash chromatography technology that employs supercritical fluid (e.g., liquid phase $CO_2$) as the main non-polar solvent in flash chromatography. FIGS. 1 and 2 illustrate a supercritical fluid CO2 flash chromatography apparatus. In varying embodiments, the apparatus has one or more of pre-chiller/supercritical fluid (e.g., CO2) pump that allows for the efficient and accurate delivery of liquid-phase supercritical fluid (e.g., CO2) in a supercritical fluid state to the apparatus up to 10,000 psi, e.g., up to 5000 psi or 2500 psi and at a flow rate of at least about 10 mls/min and up to about 250 ml/min or 300 ml/min, a secondary co-solvent pumping package that allows for polar modifier solvents (e.g., co-solvents) to be added to the flow stream in an isocratic or gradient mode (2500 psi and 100 mls/min), an injection manifold that can take the form of an injection loop or a secondary injection column for larger sample injection, a pressure equalizing vessel assembly that allows traditional flash column cartridges to be used in the apparatus up to the pressures of operation, a UV-VIS detector (other detectors optional), and a back pressure regulator (BPR) upstream of and in fluid communication with a stream selector, which is in fluid communication with the one or more cyclonic separators. The BPR brings the pressure of the flow stream from operation pressures down to ambient pressures for fraction collection in the cyclonic separators.

Generally, the chromatography systems are pressurized to pump supercritical fluid (e.g., CO2), with or without co-solvent. In varying embodiments, the system further pumps a co-solvent. When pumping a supercritical fluid mixed with a co-solvent, the co-solvent may comprise up to about 20% v/v of the fluid being pumped through the system. As shown in FIG. 1, the co-solvent is delivered through an input pump separate from the supercritical fluid input pump, and mixed with the supercritical fluid prior to delivery to the inner column of the pressure equalizing vessel. In some embodiments, the co-solvent comprises an alcohol of 3 or fewer carbon atoms (e.g., methanol, ethanol, propanol, isopropanol) or an acetate of 3 or fewer carbon atoms (e.g., methyl acetate, ethyl acetate, propyl acetate), or mixtures thereof.

3. Chiller for Pumping Supercritical and Liquified Gases a. Introduction

A system for super chilling liquid gases (e.g., including carbon dioxide, methane, ethane, propane, butane, ethylene, propylene, and ethers) and to increase pumping efficiency and consistency is provided. The chiller cools liquid gases (e.g., including carbon dioxide, methane, ethane, propane, butane, ethylene, propylene, and ethers) to between −10° C. and −40° C. has been shown to enable the use of a standard HPLC pump with increased mass flow rates at a constant set point as the temperature is reduced. The herein described system reduces the cost of pumping CO2 by allowing the use of traditional HPLC pumps, rather than highly specialized CO2 pumps.

The present systems and methods use a cascade chiller to cool the liquid CO2 to less than −10° C., e.g., in varying embodiments, less than −20° C., to minimize the variance in pump performance. The lower temperatures enable greater tolerance for the flow path in the high pressure CO2 pump head and facilitate the use of an unmodified HPLC (High Pressure Liquid Chromatography Pump). Traditional HPLC pumps are normally intended for pumping liquids; not liquid gases. There is a wide scatter in flow performance that results when the liquid is chilled to only 0° C. At room temperature conditions the variance would be greater than 30% and would render the unmodified HPLC pump completely ineffective in supercritical chromatography applications. The herein described chiller and methods allows the use of a traditional HPLC for precise metered pumping of liquid-gases, e.g., for delivery to extractors, reactors and chromatography equipment.

We have determined that extreme subcooling much improved pumping performance. The pumping mass flow rate was linearly related to speed and repeatability. In this case, the supercritical CO2 was subcooled from an ambient condition of nearly 25° C. and 52 bar to approximately −25° C. and 52 bar. This 55° C. temperature reduction resulted in the liquid CO2 conditions more closely resembling an incompressible fluid, such as water. A completely unmodified and standard HPLC pump can then be used to pump the scCO2 under very linear conditions. Such behavior is highly desirable for applications including supercritical fluid extraction, supercritical fluid solid phase extraction, supercritical fluid flash chromatography, and supercritical fluid chromatography.

The use of this hook of physics is advantageous in these applications, as it enables standard and cost-effective HPLC pumps to be used in supercritical fluid applications with highly linearly mass flow rates without the need for either elaborate compensation algorithms, sensor feedback systems involving compensation via a loss in weight measurement of the supply cylinder, direct compensation via a mass flow measure (e.g. coriolis mass meter), or the need for a booster pump to stabilize the delivery flow to the pumping system.

b. Prechiller or Chiller-HPLC Pump Assembly

Figure 3A:
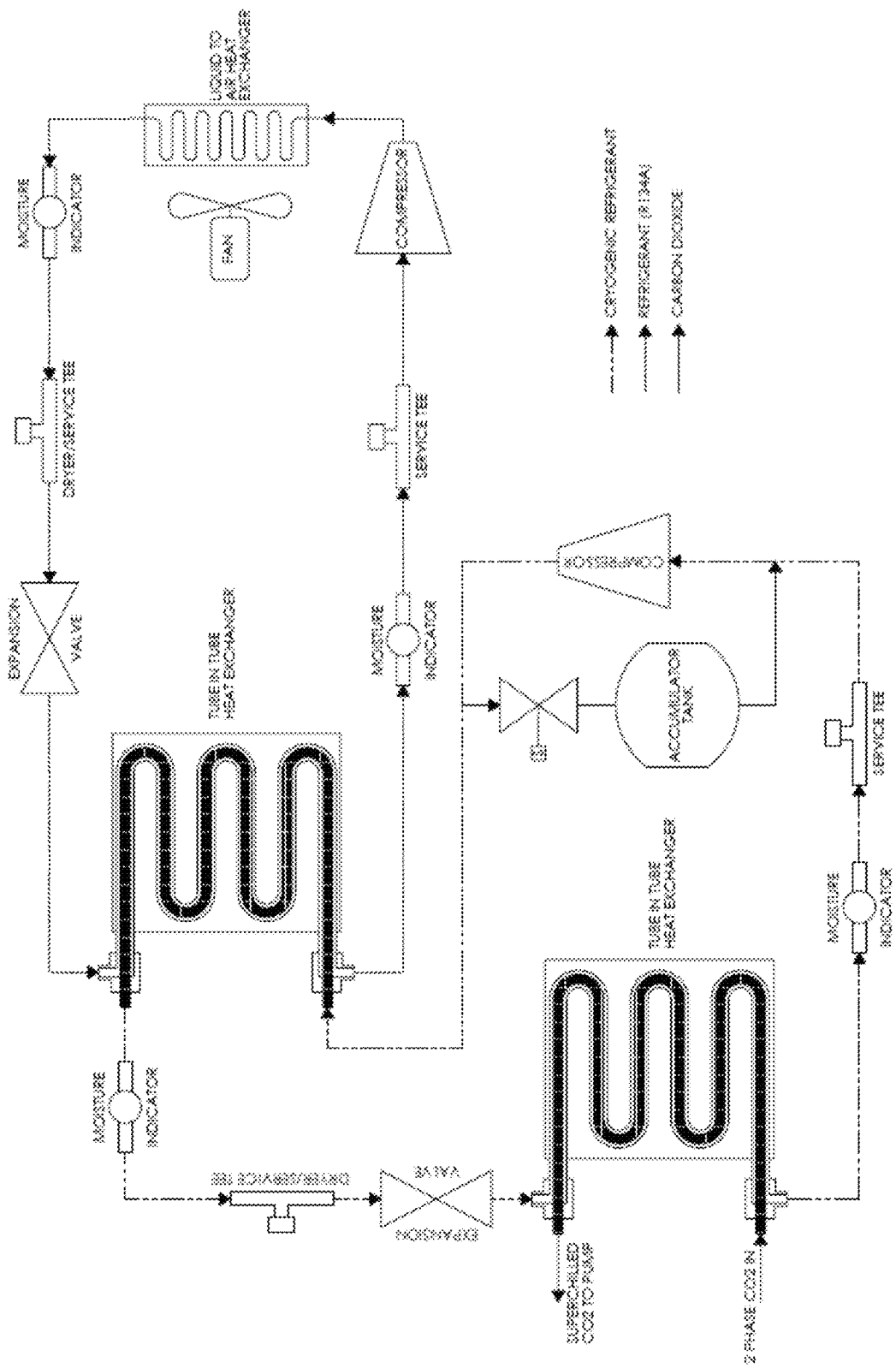
FIGS. 3A-B.

Generally, the prechiller or chiller utilizes dual refrigeration circuits with tube-in-tube heat exchangers that allow for heat exchange without an intervening heat exchange medium. FIG. 3A illustrates a block diagram of the two circuit cascade refrigeration heat exchanger present in the chiller. The two circuits are a low temperature circuit and a high temperature circuit. In such systems, the two circuits are thermally coupled at the condenser of the low temperature circuit. In fact, the condenser of the low temperature circuit is the evaporator of the high temperature circuit. To further simplify the concept, the low temperature circuit in the chiller is used to super chill the CO2 flow to its target temperature and the high temperature circuit is used to remove the heat from the low temperature circuit.

CO2 flow enters the evaporator of the low temperature circuit at bottle pressure/temperature. Said evaporator is a tube in tube heat exchanger with an inner tube made of AISI Type 316 stainless steel or similar metal suitable for exposure to CO2. Other materials of use for the inner tube include without limitation copper, brass, and Type 304 stainless steel. Heat is removed from the CO2 by the flow of cryogenic refrigerant in the outside tube which is made of copper and surrounds the inside tube. The heat exchanger is set up as a counter flow heat exchanger for greater efficiency.

The low temperature circuit is used to pull heat from the CO2 flow to chill it to the required temperature. A cryogenic refrigerant enters the suction side of the compressor and is discharged at a higher pressure. The compressor is a 1.4 CC model by Aspen. Work is done by the compressor to increase the pressure of the cryogenic refrigerant, which raises its temperature. The cryogenic refrigerant then exits the compressor on the discharge (high pressure) side and enters the low temperature circuit condenser. The low temperature circuit condenser is the same unit as the high temperature circuit evaporator. The condenser is a tube in tube heat exchanger. The cryogenic refrigerant flows through the inside tube of the heat exchanger. Heat is removed from the cryogenic refrigerant by a conventional refrigerant flowing in the outside tube which surrounds the inside tube. This heat exchanger is arranged as a counter flow heat exchanger for greater efficiency. After having the heat removed the cryogenic refrigerant flows through a moisture indicator, and then a dryer which has a built in service port. This is the high pressure side service port. After the dryer, the cryogenic refrigerant flows through an expansion valve. In this case, the expansion valve is a coiled length of capillary tube. When the cryogenic refrigerant exits the expansion valve, it is returned back to a low pressure state, which reduces the temperature before it enters the low temperature circuit evaporator. The cryogenic refrigerant flows through the outside tube of the evaporator and removes heat from the $CO_2$ flowing through the inside tube which it surrounds. Upon exit, the cryogenic refrigerant flows through a moisture indicator and a service tee before returning to the suction side of the low temperature circuit compressor. This cycle is continuous.

The high temperature circuit uses a similar flow path with one major difference. The condenser of the low temperature circuit is a fan cooled liquid to air heat exchanger. In the high temperature circuit, a conventional refrigerant enters the suction side of the compressor and is discharged at a higher pressure. The change in pressure is accompanied by a rise in temperature. The refrigerant then flows into the condenser where forced air is used to remove heat. This heat is transferred to the atmosphere and out of the system. The refrigerant then flows through a moisture indicator and a dryer with built in service port before going through the expansion valve. On exit of the expansion valve the refrigerant is returned to a lower pressure and thus lower temperature. The refrigerant then enters the evaporator. Here the refrigerant for the high temperature circuit absorbs heat from the low temperature circuit in a tube in tube heat exchanger. Upon exit the refrigerant goes through a service tee and a moisture indicator before returning to the suction side of the compressor. This cycle is continuous.

To summarize the two circuit cascade system, it is easiest to follow the transfer of heat into and then out of the system. In the case of the chiller, heat is brought into the system by a stream of $CO_2$. The removal of heat from the $CO_2$ is the ultimate goal of the system. This heat is removed by the evaporator of the low temperature circuit. The low temperature circuit is then used to transfer heat to the high temperature circuit. This happens in the high temperature circuit evaporator which is also the low temperature circuit condenser. In the final stage of heat transfer, the high temperature circuit transfers heat out of the system and into the atmosphere in the high temperature circuit condenser. In short, heat cascades from the $CO_2$ to the low temperature circuit then the high temperature circuit and finally the atmosphere.

Figure 3B:
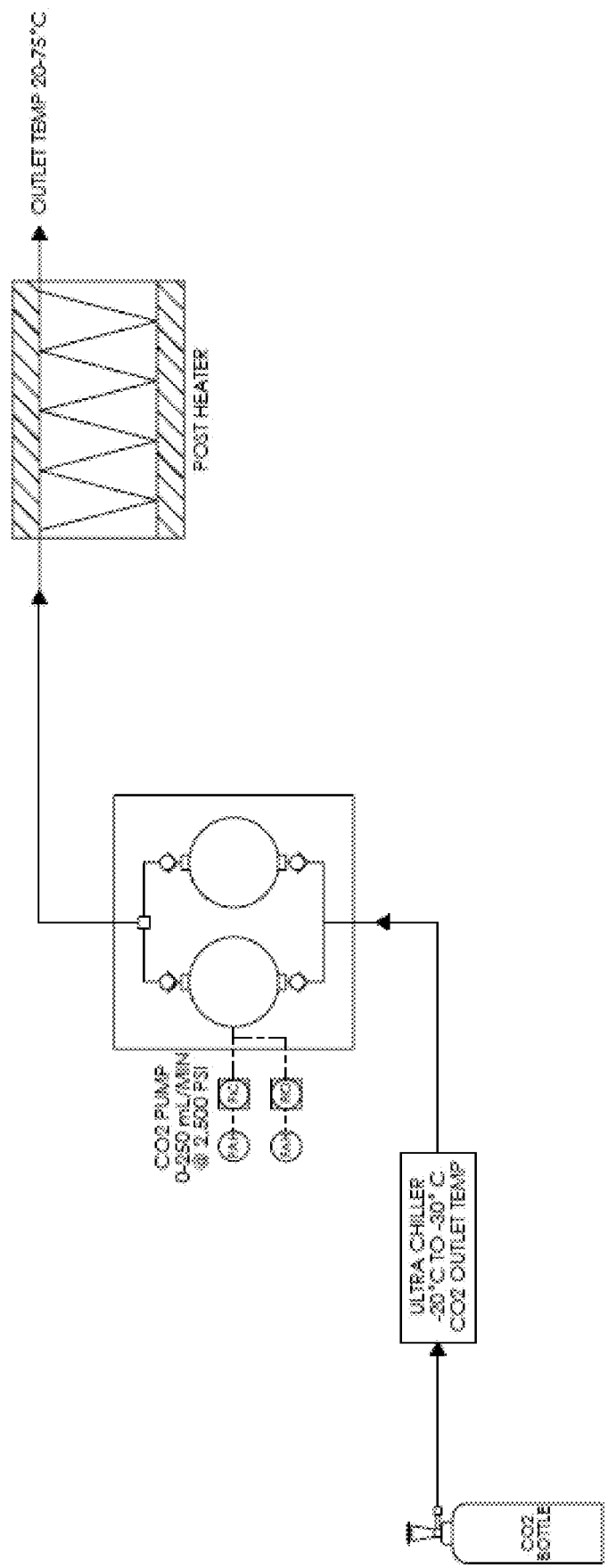

FIG. 3B illustrates the connection of the chiller to a traditional HPLC type SCF Pump with the addition of post-pump heaters to bring the fluids up to operational temperatures.

c. Embodiments of Prechiller or Chiller

In varying embodiments, the chromatography system comprises a prechiller or chiller, as described herein, upstream of a pump to cool the supercritical fluid sufficiently such that it can be pumped through a standard off-the-shelf, commercially available flash chromatography or high performance liquid chromatography (HPLC) pump. The prechiller improves the pumping performance (e.g., the consistency) for a supercritical fluid, e.g., carbon dioxide such that system mass flow rates are proportionate to pump speed.

In varying embodiments, the prechiller cools the liquid phase supercritical fluid (e.g., $CO_2$) to a temperature of about −5° C. or less, e.g., −10° C., −15° C., −20° C., −25° C., or less, e.g., but above the triple point temperature, e.g., above about −55° C., e.g., to about −40° C., −45° C. or −50° C. Such supercooling or extreme subcooling reduced in much improved pumping performance. The pumping mass flow rate was linearly related to speed and repeatability. In varying embodiments, the prechiller subcools the supercritical fluid (e.g., $CO_2$) from an ambient condition of nearly 25° C. to approximately −10° C. or lower temperatures. In varying embodiments, the system employs a 2-stage refrigerant on refrigerant chiller system to cool and liquefy the gas phase supercritical fluid. In varying embodiments, the system does not directly or separately cool the pump heads.

This minimum of 35° C. temperature reduction resulted in the supercritical fluid (e.g., liquid phase $CO_2$) conditions more closely resembling an incompressible fluid, such as water. A completely unmodified and standard HPLC pump can then be used to pump the supercritical fluid (e.g., liquid phase $CO_2$) under very linear conditions. Such behavior is highly desirable for application including supercritical fluid extraction, supercritical fluid solid phase extraction, supercritical fluid flash chromatography, and supercritical fluid chromatography.

The supercooling prechiller enables standard and cost effective HPLC pumps to be used in supercritical fluid applications with highly linearly mass flow rates with the need for either elaborate compensation algorithms, sensor feedback systems involving compensation via a loss in weight measurement of the supply cylinder, direct compensation via a mass flow measure (e.g., coriolis mass meter), or the need for a booster pump to stabilize the flow.

4. Pressure Equalizing Vessel a. Introduction

Pressure equalization assemblies and methods of use are provided. More specifically, provided is a pressure equalization assembly that enables the use of low-medium pressure columns for flash chromatography in a higher pressure supercritical fluid chromatography application. The pressure equalization assemblies allows the attachment of commercially available chromatography columns or cartridges to the cap of the vessel, e.g., via a luer lock fitting, and seals on the other end using an O-ring or gasket that is captured axially by the cap and tapered stem of said column. Sample stream pressure going through the column is balanced by external pressure applied to the same column to maintain a pressure differential that is less than the standard operating pressure of the column. In doing so, it ensures that the columns can be used without failure for high pressure supercritical fluid chromatography.

b. Embodiments of the Pressure Equalizing Vessel

In varying embodiments, the supercritical fluid chromatography system comprises a pressure equalizing vessel. The pressure equalizing vessel is designed to allow the use of commercially available or off-the-shelf low to medium pressure columns (e.g., in the range of about 14-200 psi) traditionally used in flash chromatography at the higher pressures (in the range of about 1000 psi to about 10,000 psi, e.g., in the range of about 1500-2000 psi) used in Supercritical Flash Chromatography. The pressure equalizing vessels described herein allow the use of more economical pre-packed disposable columns in Supercritical Flash Chromatography, rather than expensive high pressure columns that must be re-packed by the user.

The pressure equalization vessel described herein utilize pressure equalization to allow the low pressure columns to exceed their rated burst pressures. This is accomplished by pressurizing the outside of the column to a level that ensures that the pressure differential between the flow through the inside of the column and the equalizing pressure on the outside of the column remains within the rated pressure of the column. For example, if a column is rated at 200 psi normal operating pressure, and the user desired to run at higher pressure ranges of about 1000 psi to about 10,000 psi, e.g., 1500-2000 psi, the system would ensure that the equalizing pressure is within 200 psi of working pressure. Testing has proven this to be effective at preventing failure of the columns due to overpressure.

The pressure equalization system allows the attachment of commercially available or off-the-shelf flash chromatography columns to the cap of the vessel via a luer lock fitting, and seals on the other end using an O-ring or gasket that is captured axially by the cap and tapered stem of said column. The pressure equalizing vessel is compatible for use with any commercially available pre-packed flash chromatography cartridge, including without limitation cartridges made by Grace (grace.com), Silicycle (silicycle.com), Biotage (biotage.com), Teledyne-ISCO (isco.com), Buchi (buchi.com), Interchim Inc. (interchiminc.com), and Agilent (agilent.com). The pressure equalizing vessel does not limit the size of the inner column cartridge that can be used, but is designed to adjust and accommodate to the chromatography cartridge appropriate for a desired separation. In varying embodiments, the inner column can contain in the range of from about 4 grams to about 350 grams stationary phase media, e.g., 4 grams, 8 grams, 12 grams, 20 grams, 80 grams, 120 grams or 330 grams stationary phase media. In varying embodiments, the inner column comprises a diameter in the range of about 0.5 inches to about 3.5 inches and a column length in the range from about 3.5 inches to about 11 inches. Illustrative diameter and length sizes of the inner column include without limitation 0.94 inches diameter×3.85 inches length (4 grams stationary media); 1.38 inches diameter×4.60 inches length (12 grams stationary media); 1.77 inches diameter×6.43 inches length (40 grams stationary media); 1.99 inches diameter×9.50 inches length (80 grams stationary media); 2.18 inches diameter×10.31 inches length (120 grams stationary media); or 3.39 inches diameter×10.55 inches length (330 grams stationary media).

Sample stream pressure going through the column is balanced by external pressure applied to the same column to maintain a pressure differential that is less than the standard operating pressure of the column. In doing so, it ensures that the columns can be used without failure for high pressure supercritical fluid chromatography.

Figure 11:
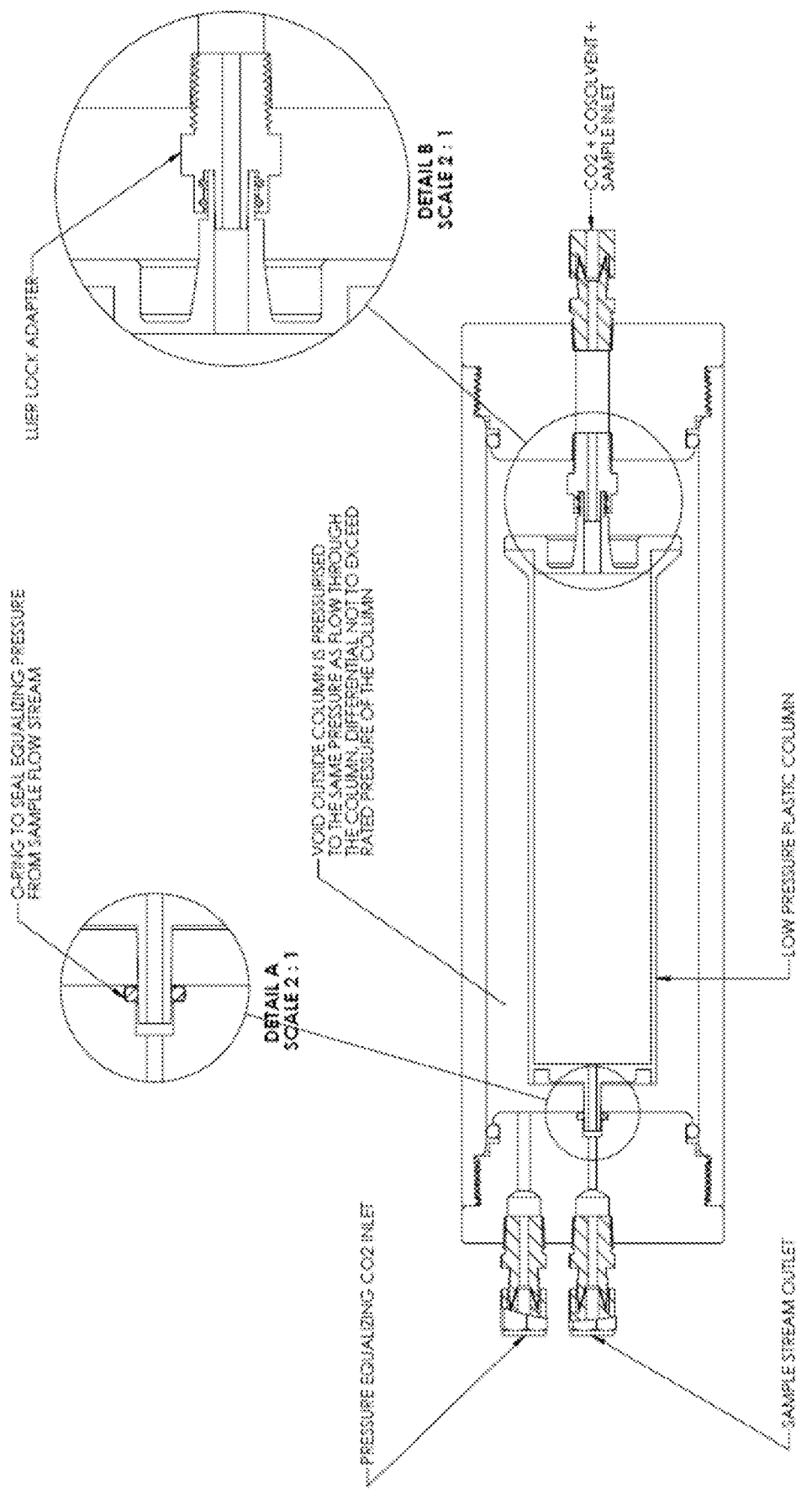
FIG. 11 illustrates a cross sectional view of the pressure equalizing vessel showing the outer pressure containment vessel and the inner chromatography cartridge or column. Insets depict the input and output attachments of the inner chromatography cartridge or column to the outer pressure containment vessel.

FIG. 11 illustrates a cross sectional view of the system. It shows the pressure containment vessel, the medium pressure column, and the methods for attaching the column to the vessel itself. The fittings of the pressure equalizing vessel can be readily adjusted to accommodate the inner column being used, wherein the standard input fitting accommodates a female luer lock on the inner column and the standard output fitting accommodates a male slip fitting on the inner column. In the embodiment depicted in FIG. 11, a luer lock connection provided on the supercritical fluid (e.g., CO2) plus optional co-solvent inlet of the column seals the outside pressure from the sample stream pressure. The luer lock adapter is shown as a threaded adapter in this print, but may also be an integral machined part of the vessel cap, or also a welded adapter. On the other end of the column, the outside equalizing pressure, and the sample stream pressure are sealed from each other using an O-ring or gasket, on the outside of the column stem. The cap of the vessel has a shelf to capture said gasket and the column stem is tapered so that it also helps capture the gasket in position by providing an axial force. This tapered stem and the luer lock on the opposite end are typical of industry standard low-medium pressure columns.

FIG. 11 also shows the inlet connection for the sample stream. This stream typically is composed of a supercritical fluid (e.g., CO2), optionally a co-solvent, and the sample to be separated. The fitting shown is a high pressure compression fitting made to seal on the outside diameter of appropriately sized high pressure tubing. The same type of fitting is used for the Sample stream outlet, and the pressure equalizing inlet. The pressure equalizing medium will typically be a supercritical fluid (e.g., CO2).

Figure 12:
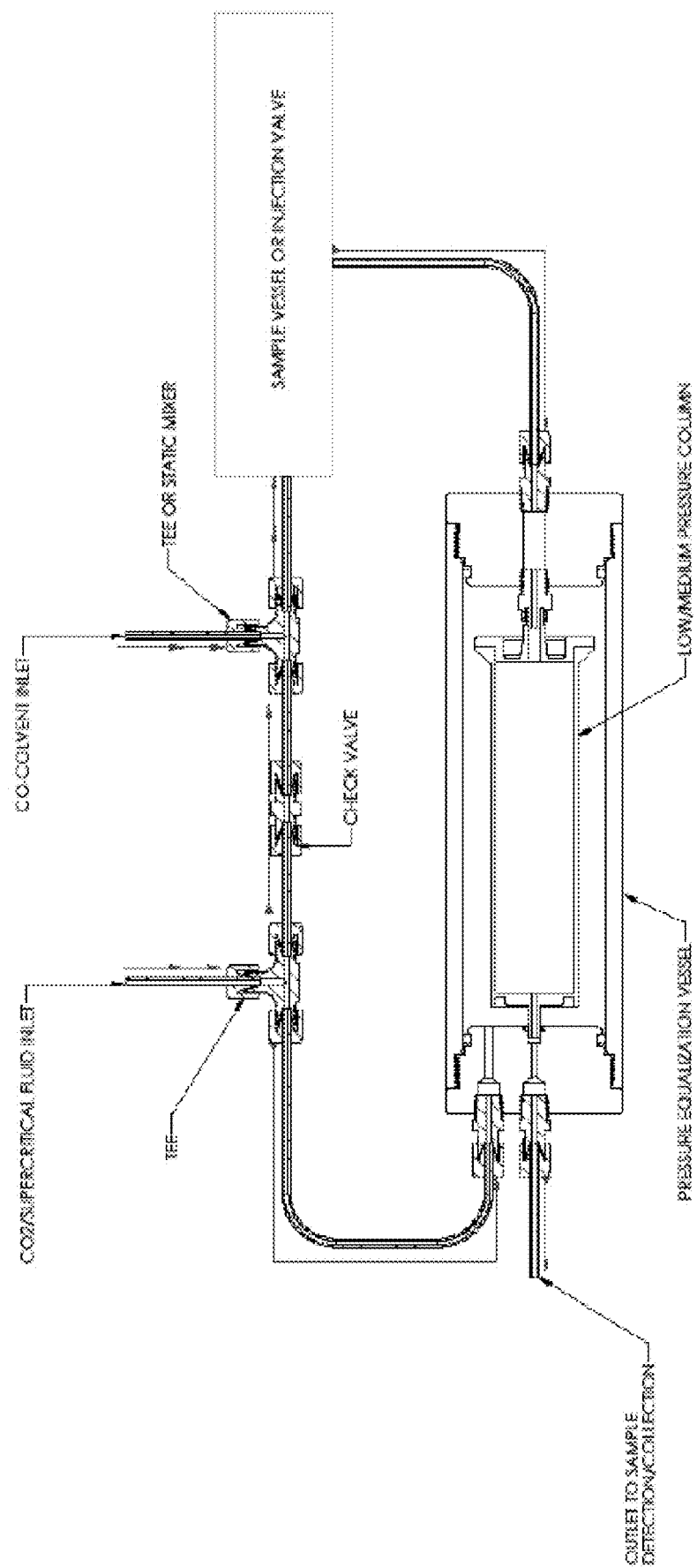
FIG. 12 illustrates a cross sectional view of the pressure containment vessel in the context of its fluid connections with an exemplary chromatography system.

FIG. 12 illustrates a cross sectional view of an example supercritical flash chromatography system with the pressure equalization system incorporated. FIG. 12 illustrates the typical inputs of supercritical fluid (e.g., CO2) and co-solvent, and shows how the system equalizes pressure in this case. Input flow of supercritical fluid (e.g., CO2) is split, one direction serves as the pressure equalizing fluid, and the other direction is used in conjunction with co-solvent to flow with the sample through the column. The system pressure is controlled by a back pressure regulator.

The check valve after the input tee for supercritical fluid (e.g., CO2) ensures that the pressure is typically greater on the outside of the low pressure column. This means that if any leaks were to occur, the leaks would occur from outside equalizing fluid, into the column. This protects the valuable samples being separated from being lost.

5. Cyclonic Separator a. Introduction

In varying embodiments, the supercritical fluid chromatography system comprises a cyclonic separator. The cyclonic separator is designed to efficiently and effectively separate sample molecules from a liquid phase or gas phase stream of a supercritical fluid, e.g., CO2. The separator is designed to accept tangential input flow, e.g., via tube compression fitting, allowing the separator to accept typical industry standard tubing. Using a tangential inlet, the flow is channeled in a cyclonic flow around the separator to separate the molecules from the gaseous flow by centrifugal force. The separator deposits the sample molecules conveniently into an attached sample collection jar, and can be completely disassembled for complete cleaning. To ensure any molecules not successfully separated by the centrifugal forces of the cyclone are not released to atmosphere, a sintered filter of an appropriate size (e.g. having a porosity grade of G-5, or a pore size in the range of about 1-16 microns) can be pressed into the exit of the cyclone, allowing only the gaseous flow to escape.

b. Embodiments of the Cyclonic Separator

The herein described cyclonic separators are designed to separate molecules from a gas phase supercritical fluid (e.g., CO2) flow and collect the molecules in a sample jar. In varying embodiments, separation procedures are performed at flow rates in the range of about 10-300 ml/min, e.g., about 250 ml/min, and at pressures in the range of about 1000-10,000 psi, e.g., about 1500-2000 psi or about 1,750 psi. The cyclonic separators can be used within a pressurized chromatography system and in fluid communication with a sample stream using compression fitting adapters and can be vented to atmosphere directly, or by hooking up a hose to the outlet. All materials of construction are suitable for use with corrosive solvents.

Other forms of cyclonic separators have been used in the past to attempt to separate a desired sample from CO2/co-solvent streams in the supercritical fluid extraction products. These have been much cruder, simpler devices typically consisting of an inlet tube that would bring the fluid/particle stream into a collection vessel at 90 degrees, the product stream would circulate around the interior diameter of the collection vessel and the particulate products and modifier co-solvents would drop out and settle at the bottom of the collection assembly and the gaseous SCF CO2 would vent through and an outlet tube. The problem with these devices was always the loss of desired product to the fluid gaseous stream on the outlet. This was because none of the devices were designed to form a true cyclonic flow, nor were they equipped with proper filtration on the outlets. By contrast, with the presently described cyclonic separators, a cyclonic flow path is induced in which the gas is forced into rotational flow around the exit tube facilitated by the tangential inlet, and is then forced into a downward spiral in towards the low pressure region by the conical section. The low pressure region is in the middle of the volume where the exit is located.

Figure 13:
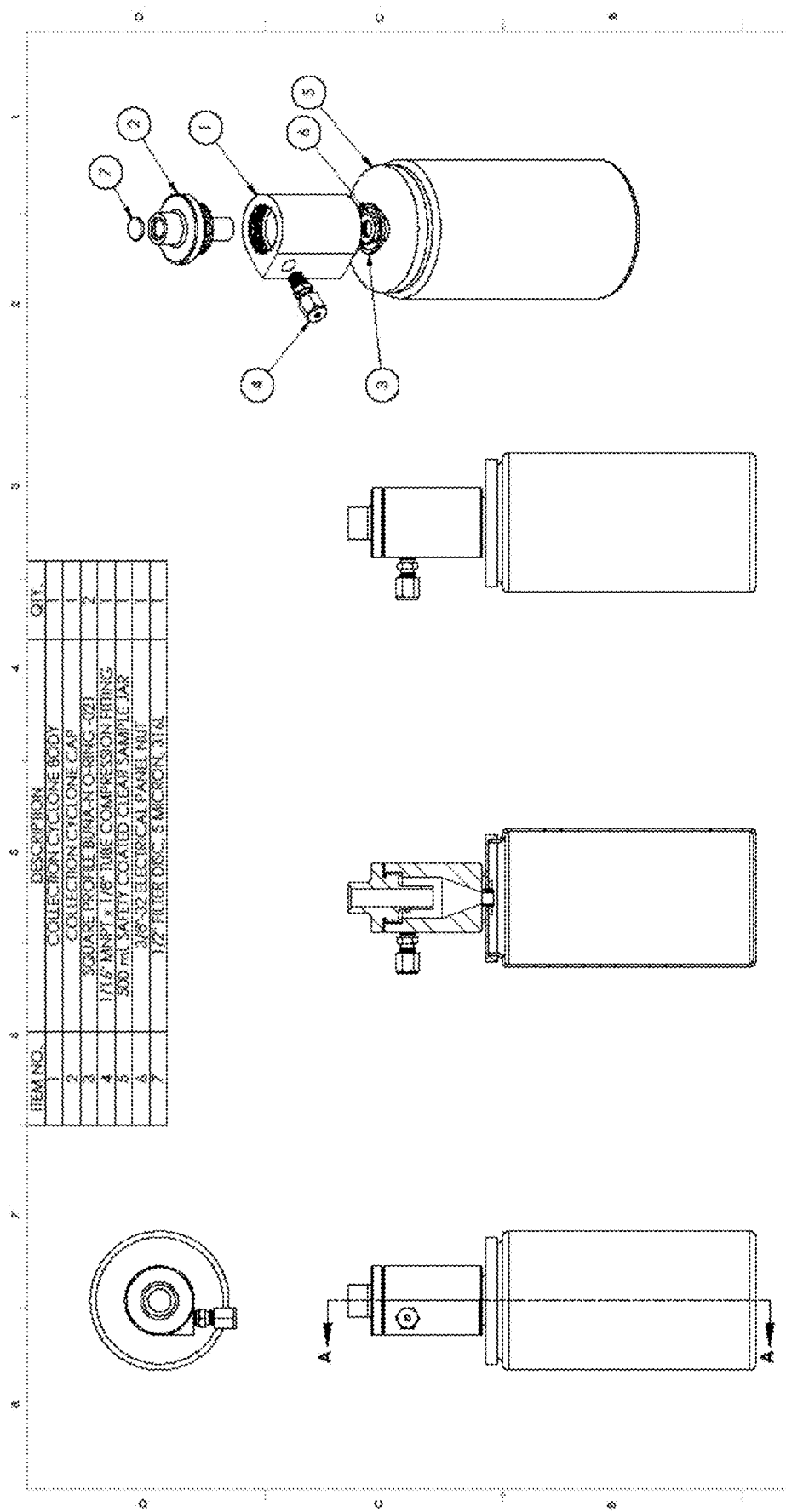
FIG. 13 illustrates an assembly drawing of the system, including a breakdown of the parts and quantities required.

FIG. 13 illustrates an overall assembly drawing of the cyclonic separator and collection assembly. The cyclone body is connected to the fluid stream using a National Pipe Thread (NPT)×compression adapter. In this illustrated assembly, the compression fitting is sized for ⅛" tube and the NPT fitting is 1/16". Compression fittings sized in the range of about 1/16 inches to about ¼ inches find use. The cyclone cap threads into the top of the cyclone body and seals against an O-ring. This ensures that pressure is not lost through the threads. The cap has a sintered filter pressed into the exit to ensure that any sample molecules that may not have been separated by the vortex flow are captured and not released to atmosphere. Pore sizes of the sintered disc can be sized for particular compounds. In the illustrated iteration, sintered filter having a porosity grade G-5 is used (1-16 microns pore size). In varying embodiments, sintered filters with G-0 to G-5 porosity grade find use (G5=pore size in the range of about 1-16 microns; G4=pore size in the range of about 10-16; G3=pore size in the range of about 16-40 microns; G2=pore size in the range of about 40-100 microns; G1=100-160 microns; and G0=pore size in the range of about 160-250 microns).

The cyclone body can be configured to be adapted to many standard collection jars. In the embodiment illustrated in FIG. 13, a 500 mL glass collection jar is used. The cyclone body can have a threaded bottom exit for attachment and sealing to the collection jar. The cap of the jar can have a through hole, which allows the cyclone body to be secured to the cap using a nut. This connection can be sealed using an O-ring, as illustrated.

Figure 14:
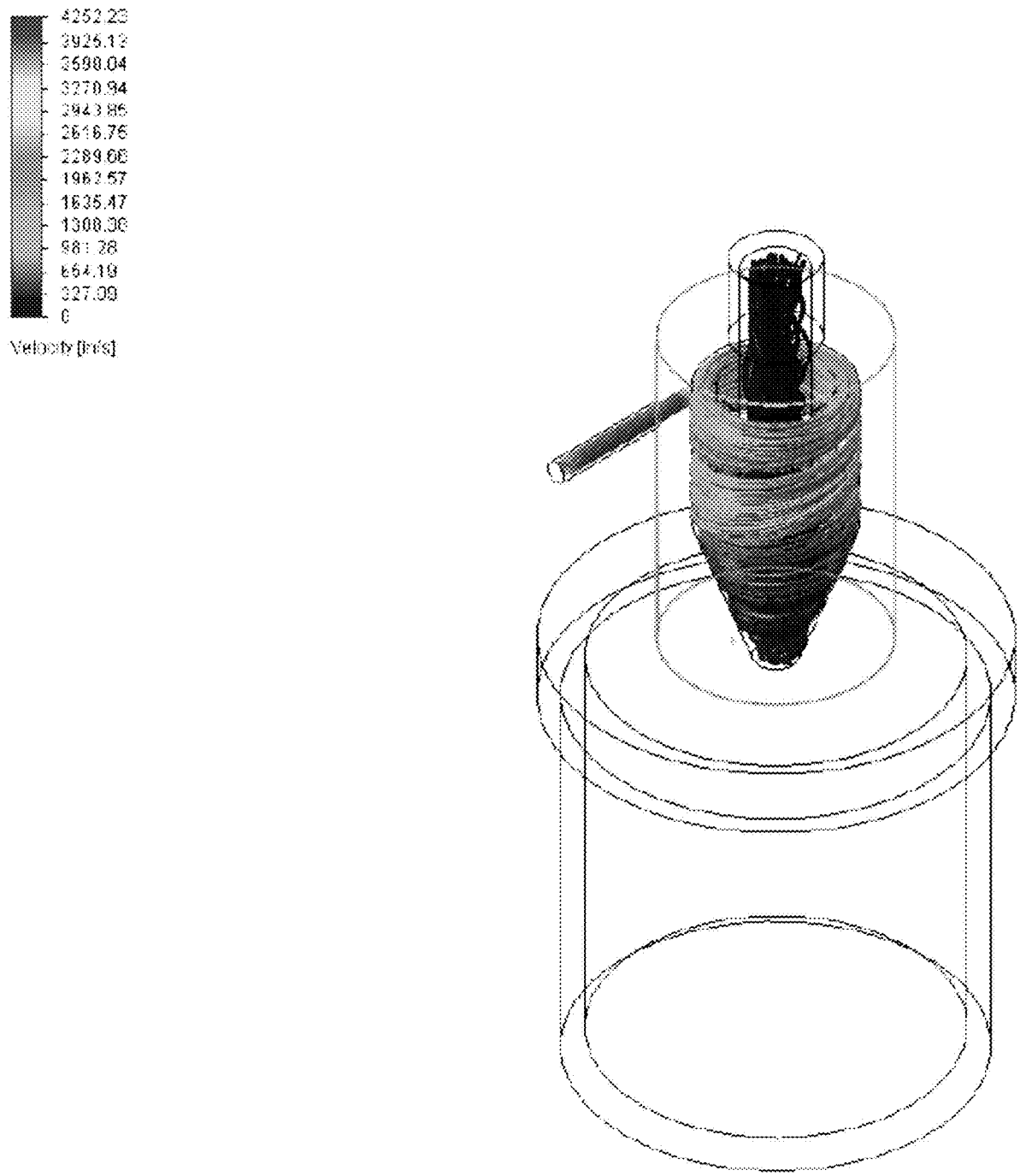
FIG. 14 illustrates a CFD visualization of the streamlines of the gas flow.

FIG. 14 illustrates the result of a Computational Fluid Dynamics (CFD) streamline study done to optimize the geometry of the cyclone at 250 mL/min @1,750 psi of supercritical CO2 flow. When the CO2 flow reaches the cyclone, it is no longer at such high pressures because the cyclone is open to atmospheric pressure. Because of this, the mass flow rate was calculated and then used to determine the velocity of the stream entering the cyclone. The shapes utilized have been done so to properly function with the parameters of the particular CFD program. Though the appearance may differ slightly from the assembly in FIG. 13, the internal geometry of the cyclone body is the same. The stream lines pictured illustrate the path and velocity of the fluid flow. The colors vary from red to blue, with red indicating the highest stream velocity, and blue indicating the lowest stream velocity. Most importantly, FIG. 14 illustrates the downward spiral, substantially non-overlapping stream lines typical of an optimized cyclonic separator.

As illustrated in FIG. 14, flow enters the cyclone body tangential to the inside diameter. The flow then begins to rotate around the exit tube of the cyclone. The centrifugal forces exerted on the molecules in the stream lines send the molecules outwards to the wall of the cyclone body, where a boundary layer keeps the streamlines from recollecting the molecules. The molecules are then free to fall to the bottom of the collection assembly. As the stream lines travel to the bottom of the cyclone body and hit the conical section, the velocity slows and the pressure increases. This forces the streamlines up the exit tube which is a low pressure escape from the higher pressure conical section.

Figure 15:
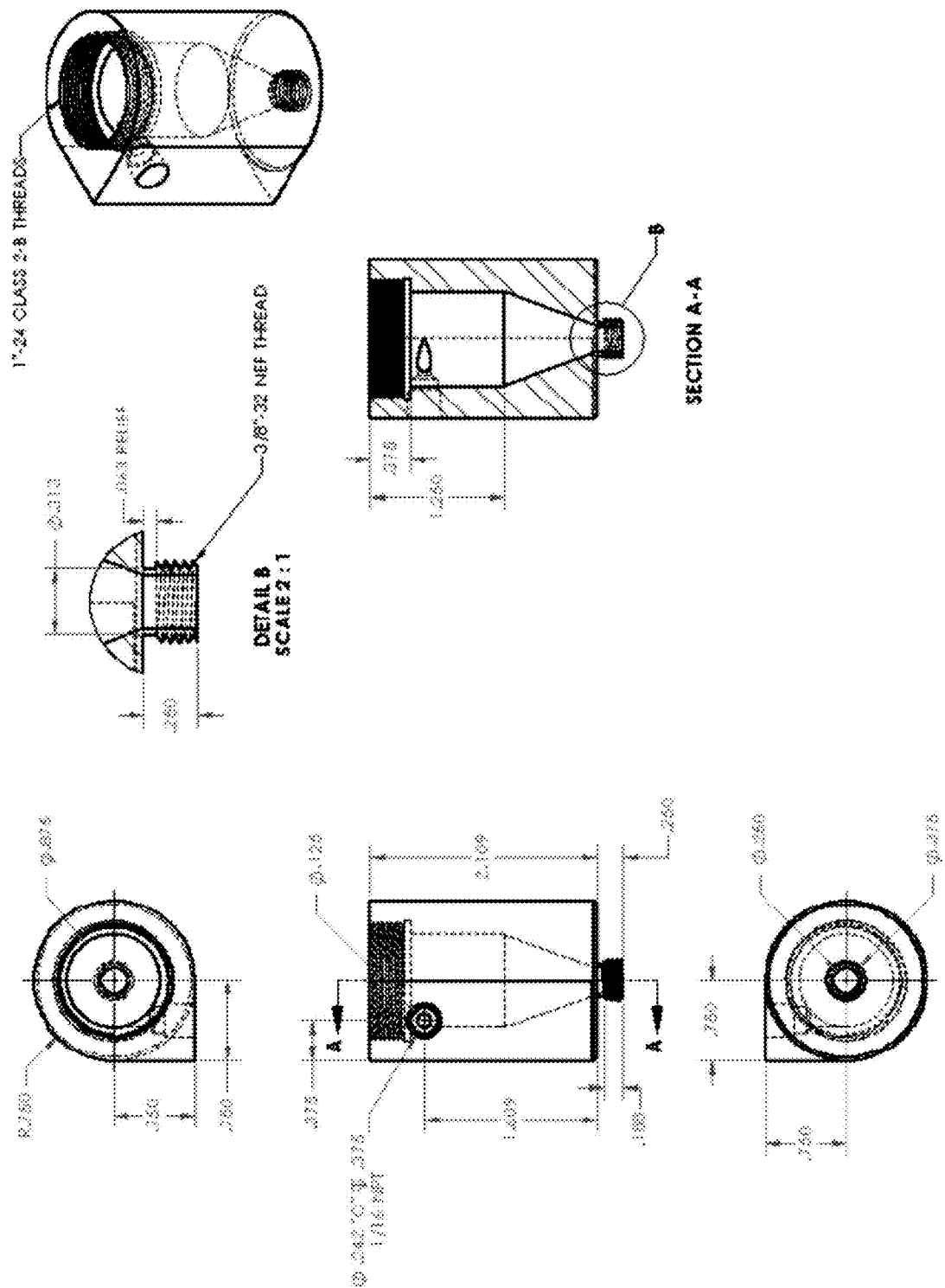
FIG. 15 illustrates a manufacturing print of the Collection Cyclone Body.

FIG. 15 illustrates the manufacturing print released to the machine shop for the current revision of the cyclone body. All dimensions and information pertinent to the manufacturing of the part are present. In the illustrated embodiment, the threads used to secure the cap to the body are the 1"-24 Class 2-B threads. Thread size is determined by the body of the cyclone, wherein the thread size and conformation are selected to withstand pressure and secure the cap. Generally, the threads are larger than the inside diameter of the cyclone body. In the illustrated embodiment, the body is secured to the collection vessel using a ⅜"-32 National Extra Fine (NEF) thread. The function of the cyclone is not dependent on these threads, they were selected to aid in manufacturing and assembly.

Figure 16:
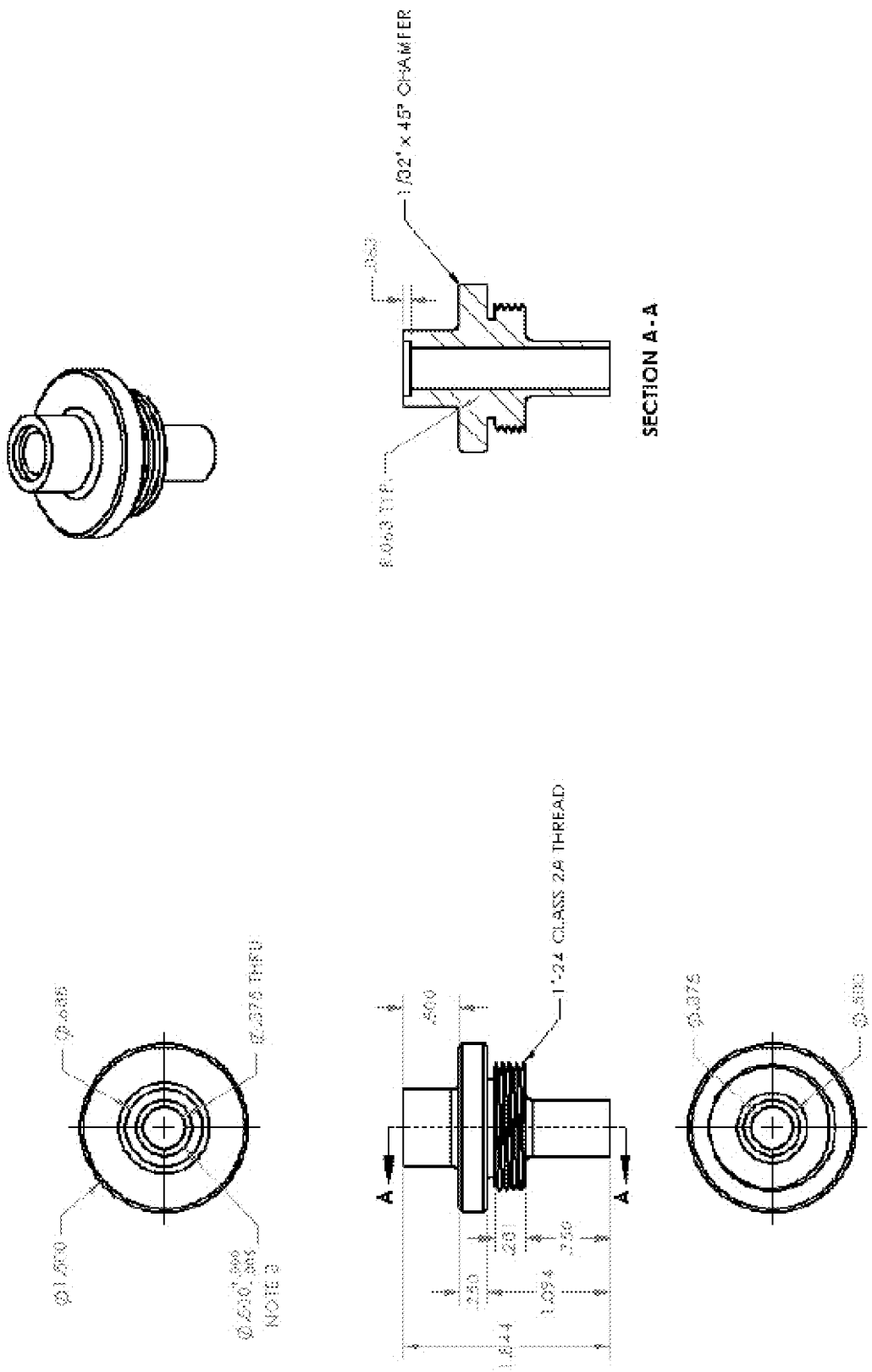
FIG. 16 illustrates a manufacturing print for the Collection Cyclone Cap.

FIG. 16 illustrates configurations of the cyclone cap. In the illustrated embodiment, the cyclone cap is secured to the cyclone body via screw threads. The ledge at the top the cap allows for a sintered filter to be pressed into the cap.

Figure 17:
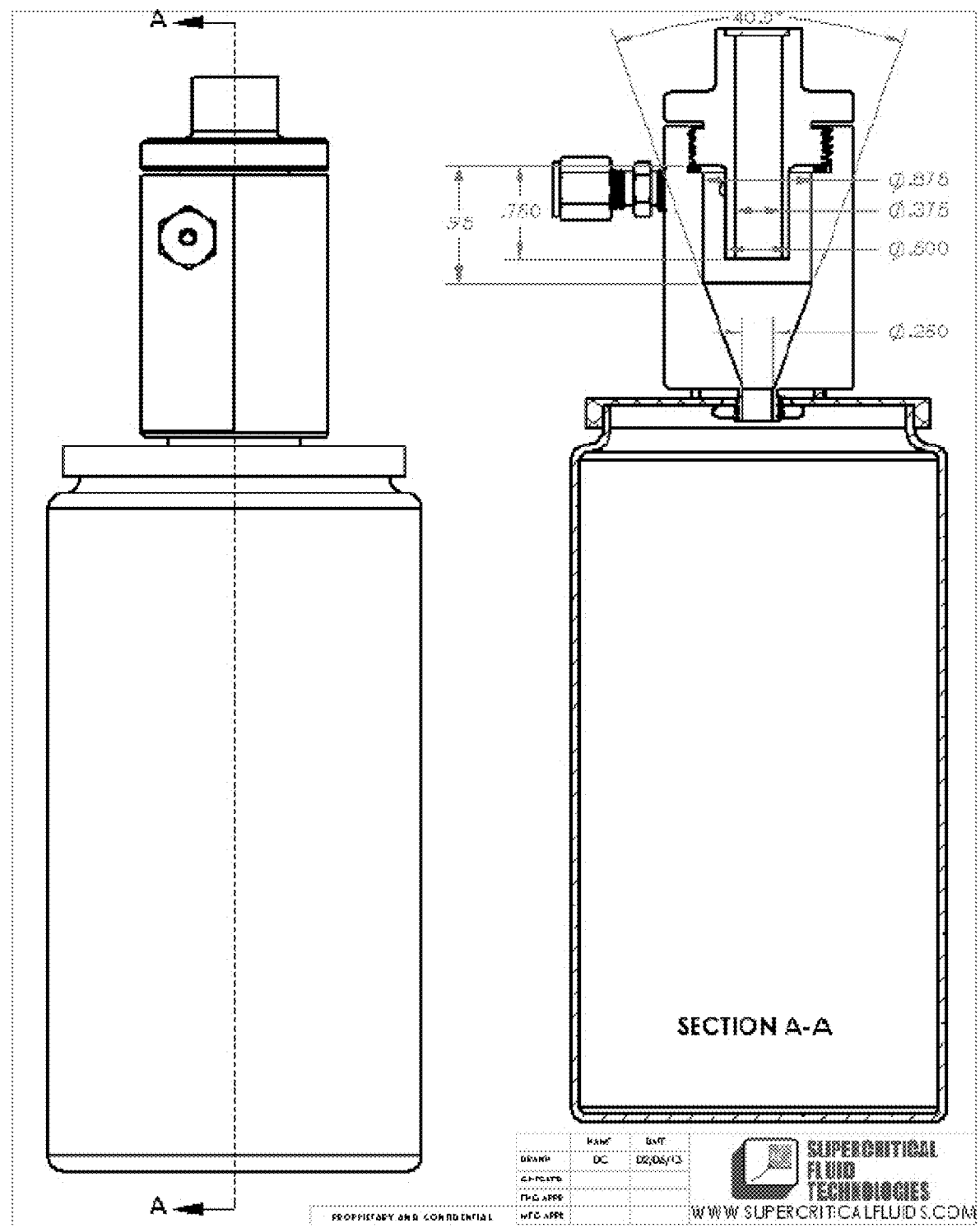
FIG. 17 illustrates a detailed internal geometry of the Collection Cyclone Assembly.

FIG. 17 illustrates the internal dimensions of the cyclone. These dimensions were honed by using CFD visualization of streamlines, as illustrated in FIG. 14. Dimensions important to the functionality include the ratio of the diameter of the outer circumference to the inner diameter of the mid-height of the funnel in the range of about 3 to about 4, e.g., about 3.5. In varying embodiments, the funnel has an angle in the range of about 30° to about 60°, e.g., in the range of about 35° to about 55°, e.g., an angle of about 30°, 35°, 40°, 45°, 50°, 55°, 60°. The illustrated embodiment depicts a 0.875 diameter to 0.250 diameter ratio (e.g., a ratio of 3.5) along with a 40 degree funnel angle. A further important dimension includes the dimensions of the protrusion at the bottom of the cap. Generally, the depth of protrusion at the bottom of the cap extends below the tangential inlet In varying embodiments, the depth of protrusion at the bottom of the cap extends, e.g., in the range of about 0.5 inches to about 1 inch, e.g., in the range of about, 0.6 inches to about 0.9 inches, e.g., about 0.50, 0.55, 0.60, 0.65, 0.70, 0.75, 0.80, 0.85, 0.90, 0.95 or 1.0 inches. This zone represents a part of the internal geometry of the cyclone collection assembly (see, FIG. 16).

6. Methods of Separating Molecules

Further provided are methods of performing high pressure separation and/or extraction procedures using a flash chromatography system, comprising employing the chiller or prechiller, as described above and herein. The chromatography systems comprising a pressure equalizing vessel, as described herein, are useful for the separation of molecules that can be separated using liquid chromatography, e.g., flash chromatography employing commercially available off-the-shelf column cartridges and off-the-shelf HPLC positive displacement pumps. Generally, molecules that can be successfully separated when employing a supercritical fluid solvent have a higher density than the supercritical solvent, for example, the molecules may have a higher density than supercritical, liquid phase and/or gas phase supercritical fluid (e.g., CO2). In varying embodiments, the molecules to be separated in the presently described chromatography systems comprising a cyclonic separator are small organic compounds, peptides, polypeptides, lipids, carbohydrates, nucleic acids and/or polynucleotides. In varying embodiments, the molecules to be separated can have a molecular weight in the range of about 40 daltons (Da or 40 gram/mol) to about 1,000,000 Da (g/mol), or more, e.g., in the range of about 100 Da (g/mol) to about 10,000 Da (g/mol), e.g., in the range of about 100 Da (g/mol) to about 5,000 Da (g/mol).

In varying embodiments, the methods entail inputting a sample to be separated that is dissolved or suspended in a supercritical fluid (e.g., CO2), with or without co-solvent, into the inner column of the pressure equalizing vessel assembly. In varying embodiments, separation procedures are performed at flow rates in the range of about 10-300 ml/min, e.g., about 250 ml/min, and at pressures in the range of about 1000-10,000 psi, e.g., about 1500-2000 psi or about 1,750 psi. The interspace of the pressure equalizing vessel surrounding the inner column is also filled with supercritical fluid at a pressure such that the pressure differential between the pressure within the interspace and the pressure within the inner space of the inside column is less than the pressure rating of the inner column (e.g., less than about 14-200 psi). Molecules in the sample are separated according to well-known principles of liquid chromatography using commercially available and off-the-shelf flash chromatography cartridges or columns packed with solid phase media commonly used in the art.

EXAMPLES

The following examples are offered to illustrate, but not to limit the claimed invention.

Example 1

Mass Flow Rates Vs. Temperature Employing the Chiller

Figure 4:
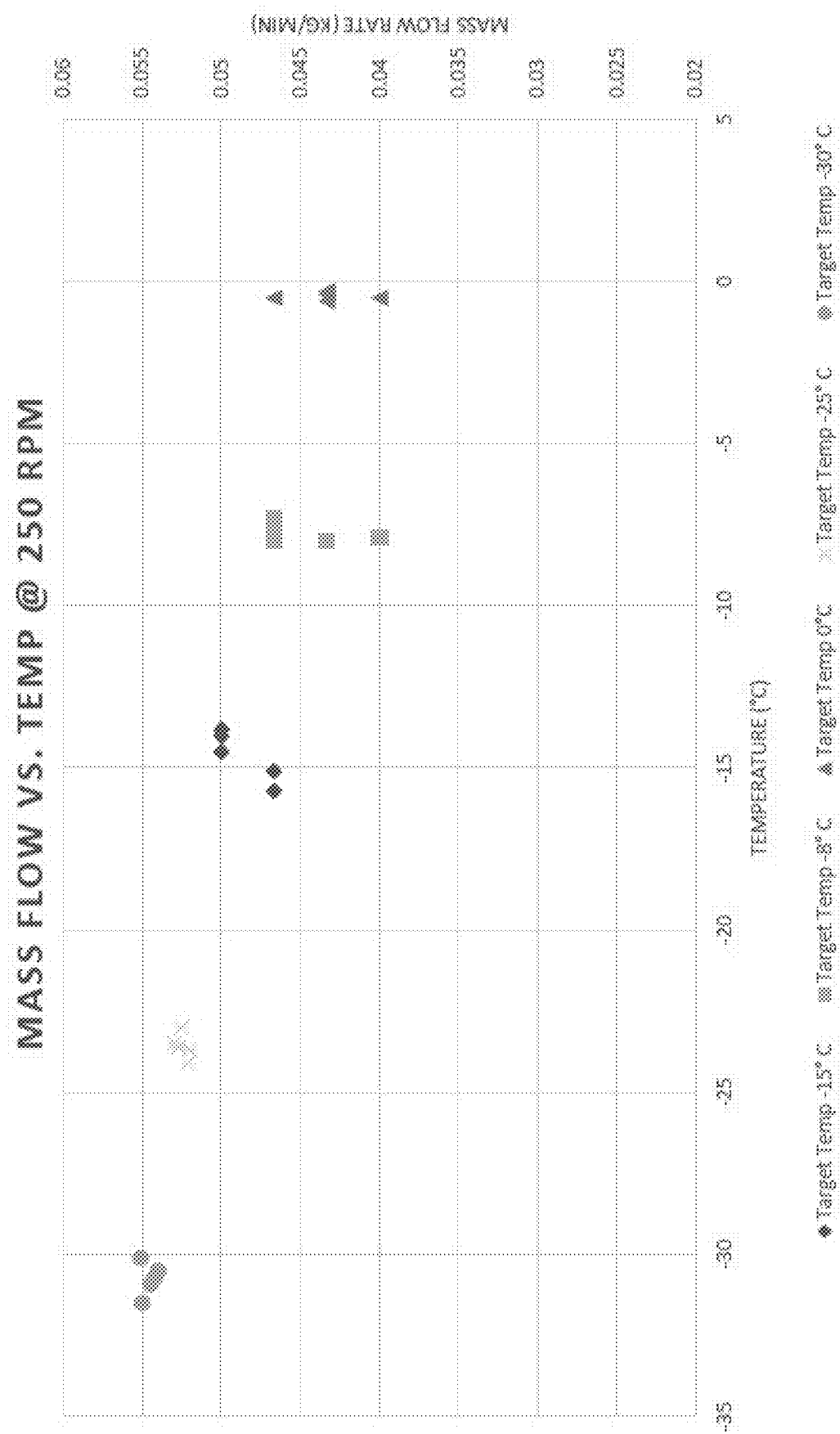
FIG. 4 illustrates a plot of mass flow rate vs. temperature at a set RPM of 250.

FIG. 4 illustrates test data for mass flow rate vs. temperature at 250 rpm pump speed. The data is focused around the temperature of −10° C., where pumping consistency increases and mass flow rate and pumping efficiency also begin to increase with decreasing temperatures. At an average temperature of 0.3° C., average mass flow rate was 0.0433 kg/min with a standard deviation of 0.0024. At an average temperature of −7.95° C., average mass flow rate was 0.0447 kg/min with a standard deviation of 0.0030. At an average temperature of −14.75° C., average mass flow rate was 0.0487 kg/min with a standard deviation of 0.0018. At an average temperature of −23.53° C., average mass flow rate was 0.0525 kg/min with a standard deviation of 0.0004. At an average temperature of −30.78° C., average mass flow rate was 0.0546 kg/min with a standard deviation of 0.0005. All tests were performed at a constant RPM of 250, with a target pressure of 2,000 psi and set point flow rate of 13 mL/min. The data shows a trend of increasing mass flow rate below −10° C. and decreased variation.

Figure 5:
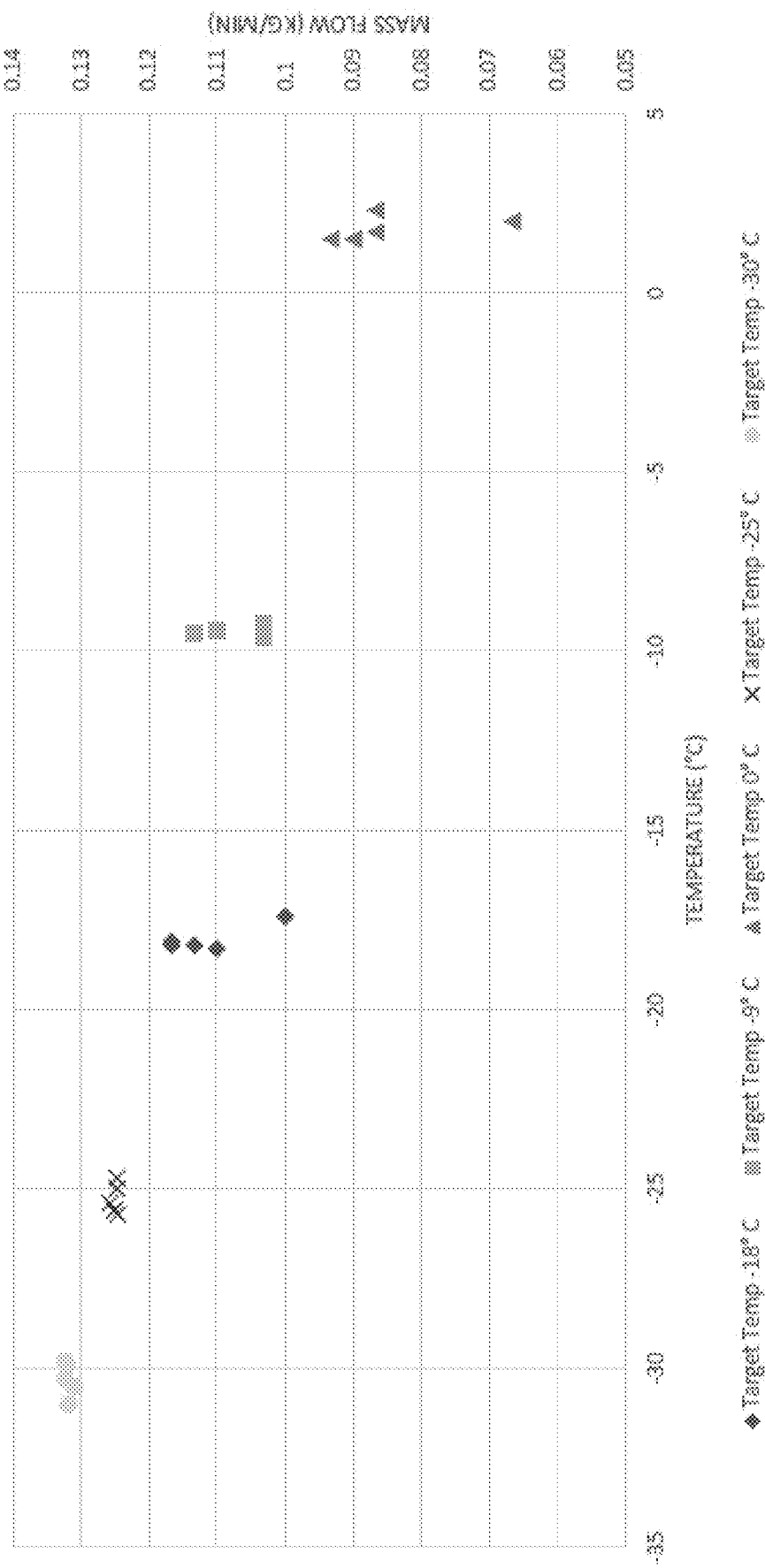
FIG. 5 illustrates a plot of mass flow rate vs. temperature at a set RPM of 500.

FIG. 5 illustrates test data for mass flow rate vs. temperature at 500 rpm pump speed. The data is focused around the temperature of −10° C., where pumping consistency increases and mass flow rate and pumping efficiency also begin to increase with decreasing temperatures. At an average temperature of 1.3° C., average mass flow rate was 0.0847 kg/min with a standard deviation of 0.0104. At an average temperature of −9.23° C., average mass flow rate was 0.1067 kg/min with a standard deviation of 0.0047. At an average temperature of −17.88° C., average mass flow rate was 0.1113 kg/min with a standard deviation of 0.0069. At an average temperature of −25.28° C., average mass flow rate was 0.125 kg/min with a standard deviation of 0.0005. At an average temperature of −30.37° C., average mass flow rate was 0.132 kg/min with a standard deviation of 0.0005. All tests were performed at a constant RPM of 500, with a target pressure of 2,000 psi and set point flow rate of 33 mL/min. The data shows a trend of increasing mass flow rate below −10° C. and decreased variation.

Figure 6:
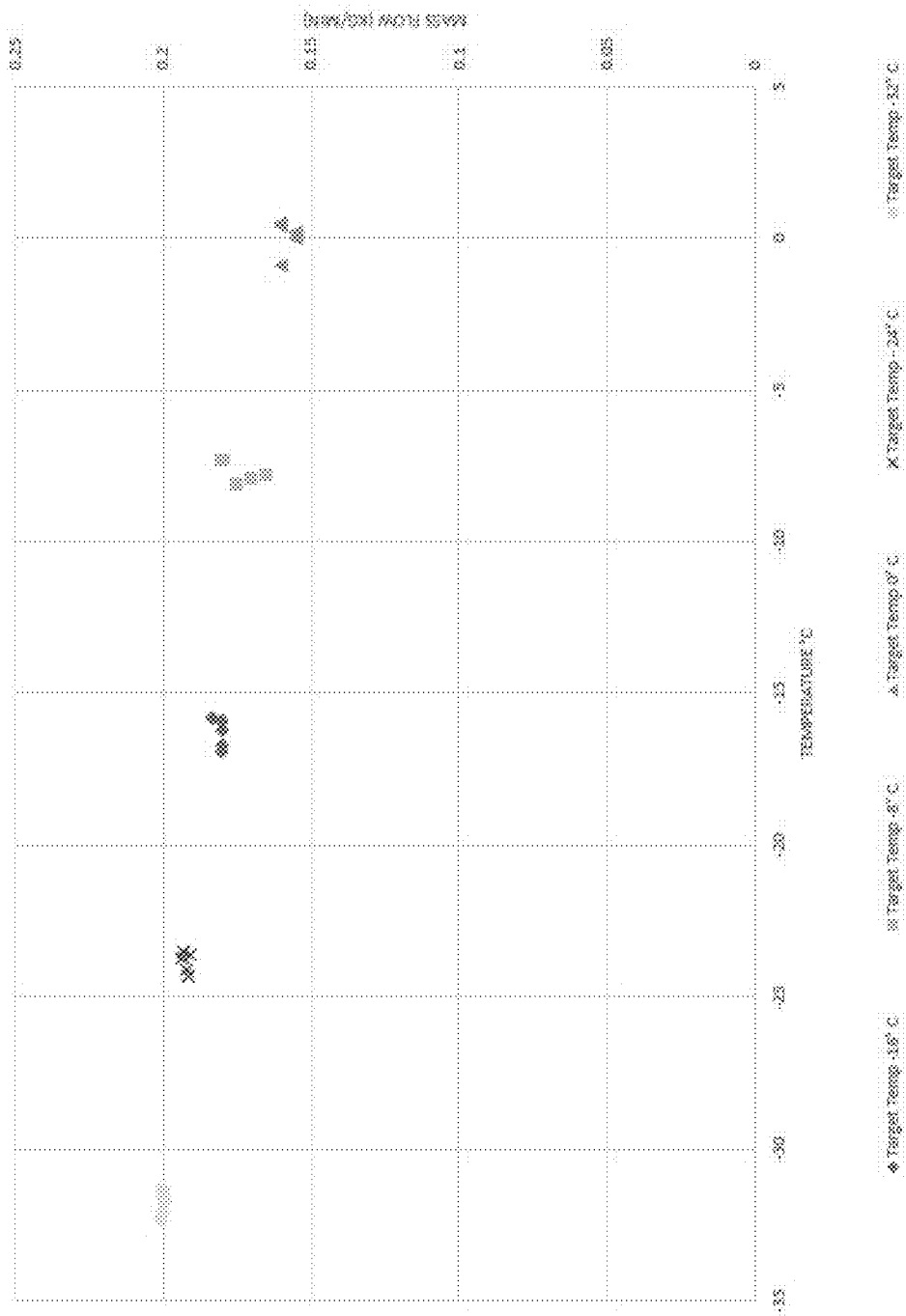
FIG. 6 illustrates a plot of mass flow rate vs. temperature at a set RPM of 750.
Figure 7:
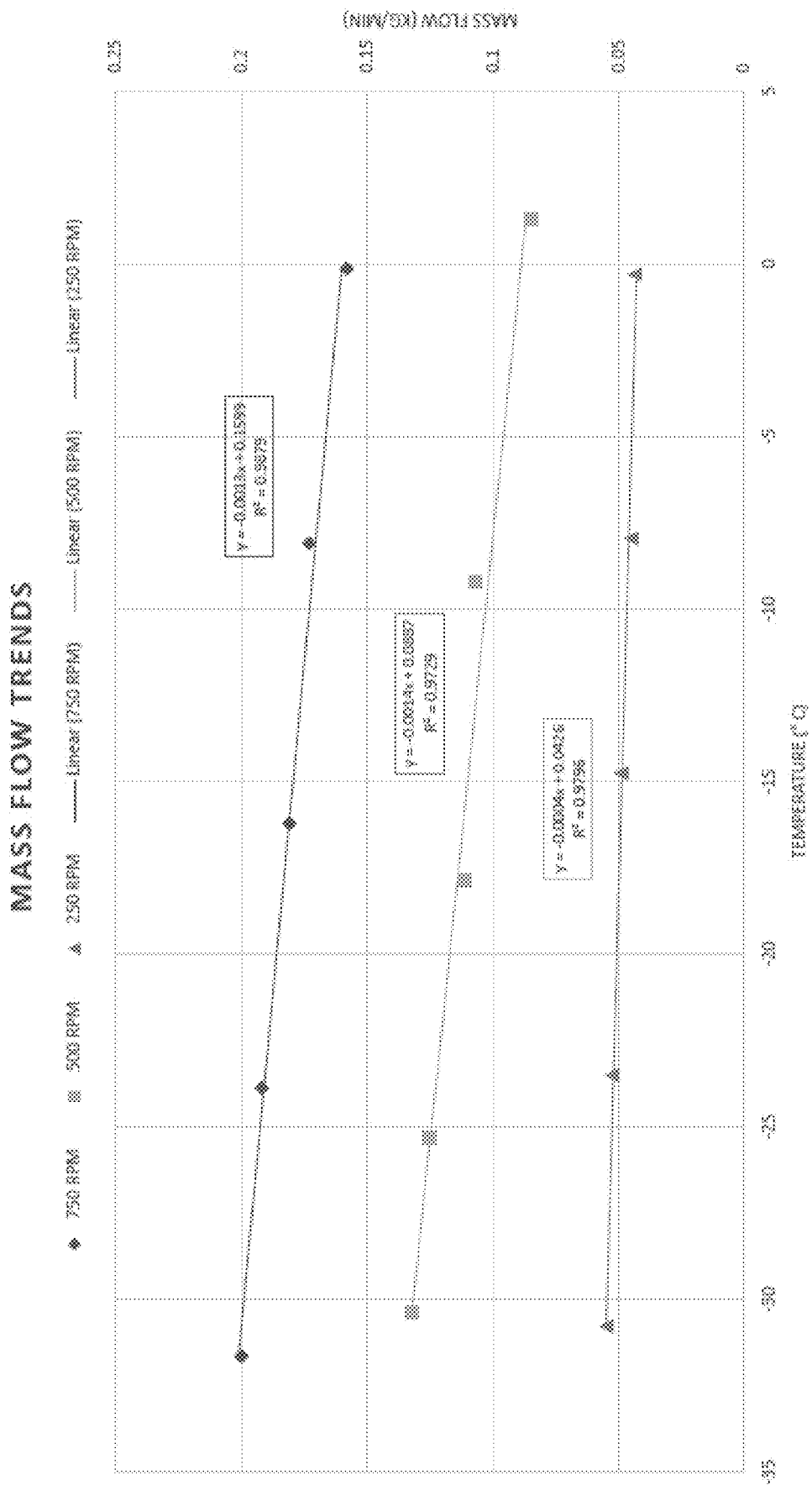
FIG. 7 illustrates trend lines for mass flow vs. temperature at the set RPMs of 250, 500 and 750.
Figure 8:
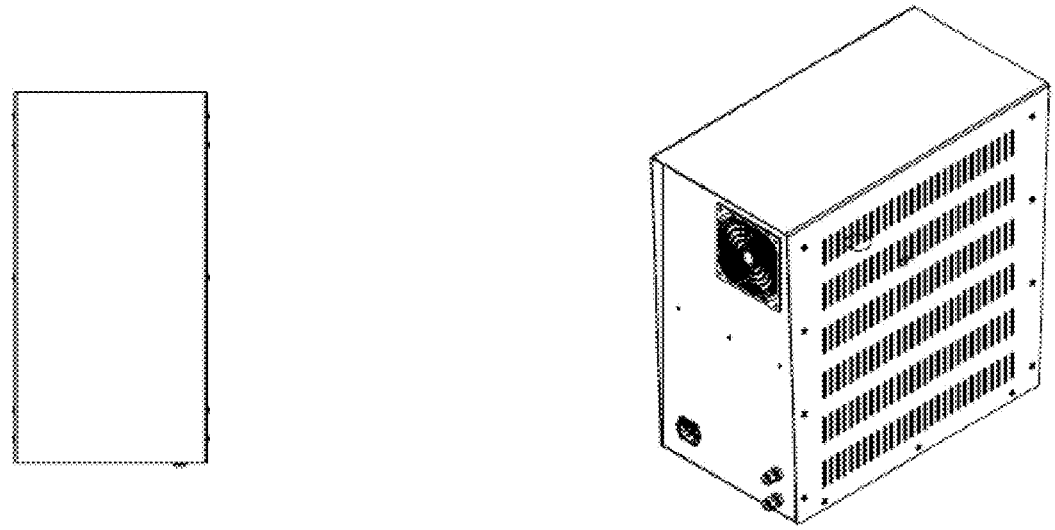
FIG. 8 illustrates an assembly drawing of external views of a production prototype of the chiller. Enclosure (1). Power entry (3). Fan guard (23). Bulkhead union (25).
Figure 8:
Figure 9:
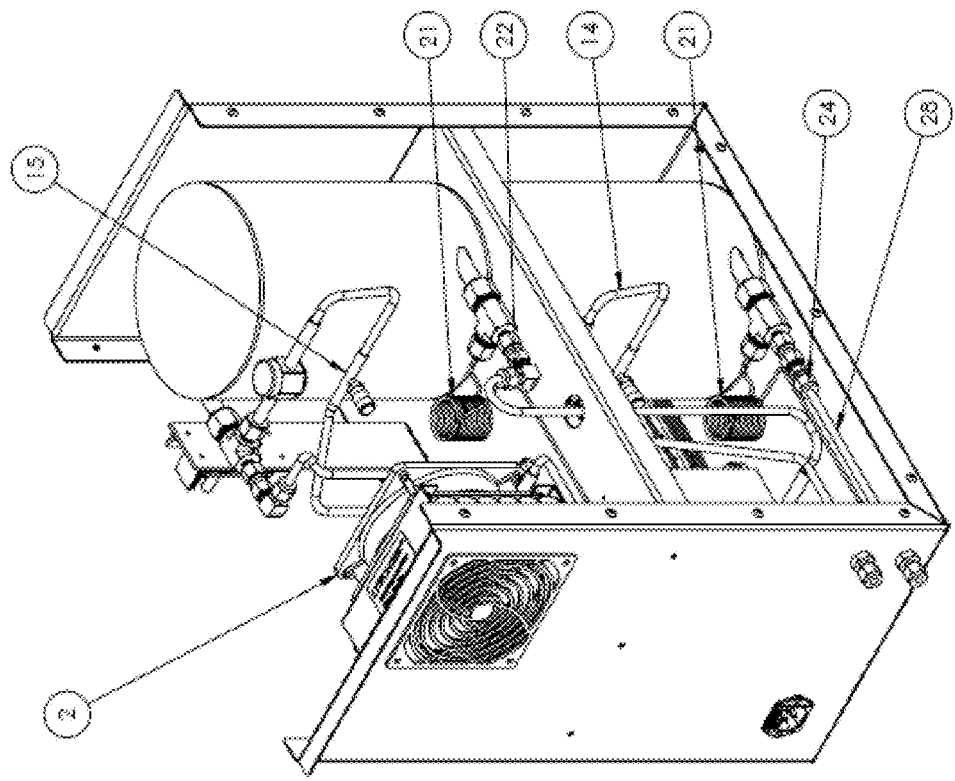
FIG. 9 illustrates an assembly drawing of internal views of a production prototype of the chiller. Fan-cooled heat exchanger (2). Tube-in-tube heat exchanger (5). Sight glass; moisture indicator (12). Sight glass to service Tee Tube (14). Access valve (15). Service Tee to suction inlet tube (16). Capillary tube winding (21). Union elbow with tube fitting (22). Union coupling with tube fitting (24). Cryo compressor suction inlet tube (27). Liquid gas outlet tube (28). High capacity compressor drive (30). Mounting bracket (31). Drive board—compressor (32). 1.4 CC compressor (33).
Figure 9:
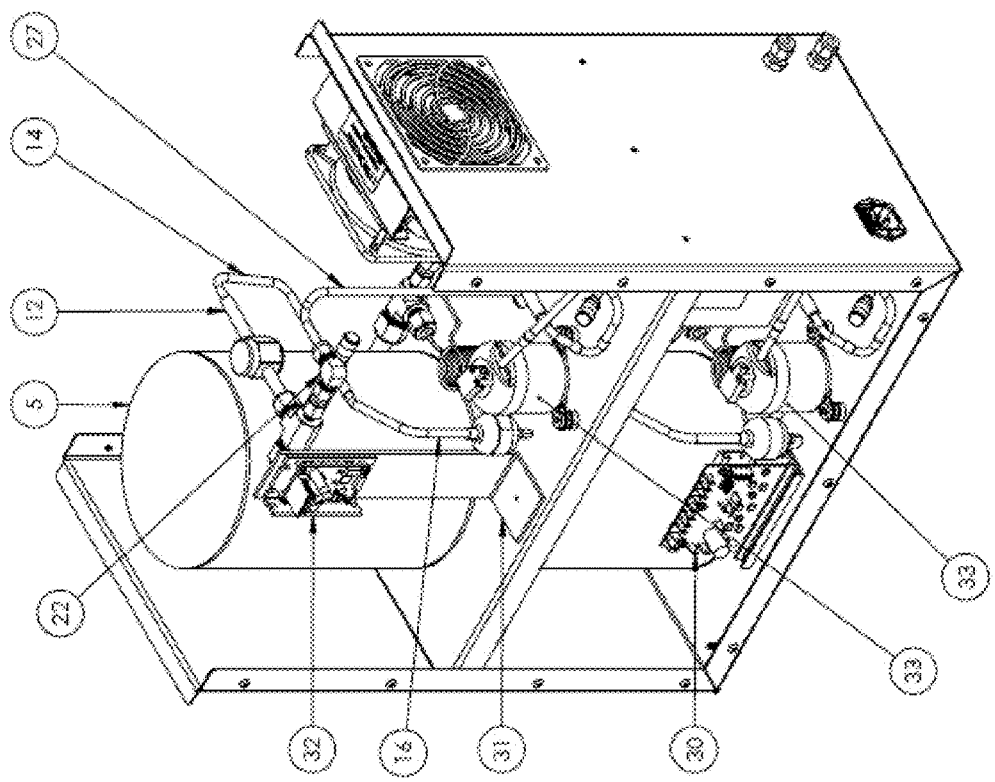
Figure 10:
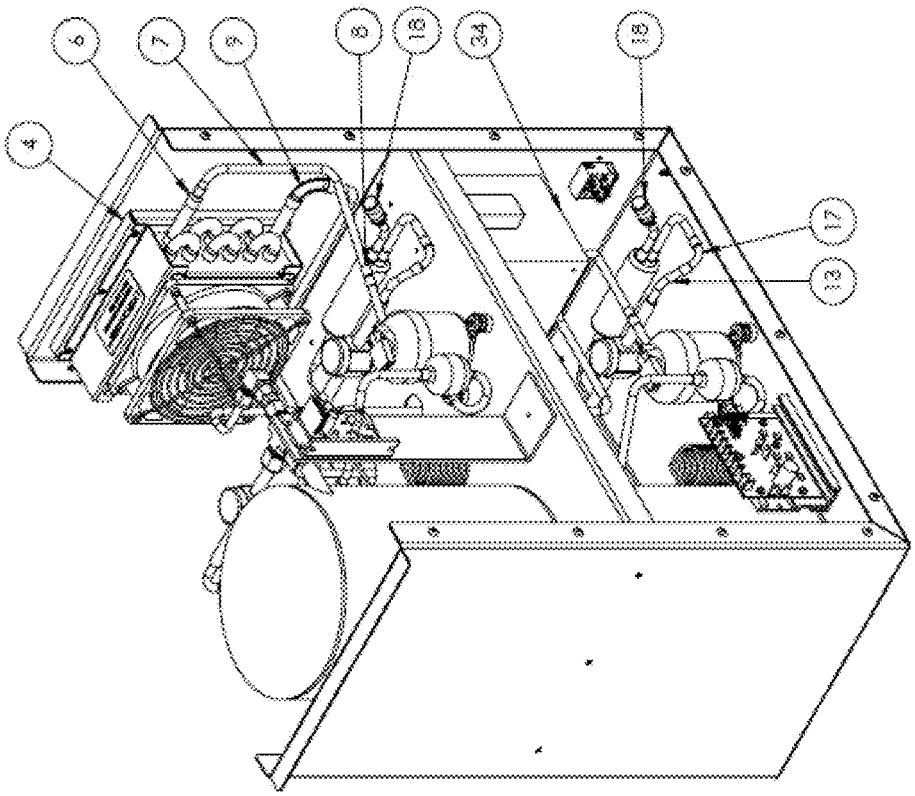
FIG. 10 illustrates an assembly drawing of internal views of a production prototype of the chiller. Fan mounting bracket (4). Reducing coupling (6). Compressor to condensing tube (7). Solder connection; copper fitting (8). 90 degree long elbow solder connection (9). Condenser to sight port tube (10). Copper tube, 45 degree elbow (13). 90 degree long elbow solder connection (17). Dryer, liquid line with service port (18). Down tube—condenser side (26). Liquid gas inlet tube (29). Power supply (34).
Figure 10:
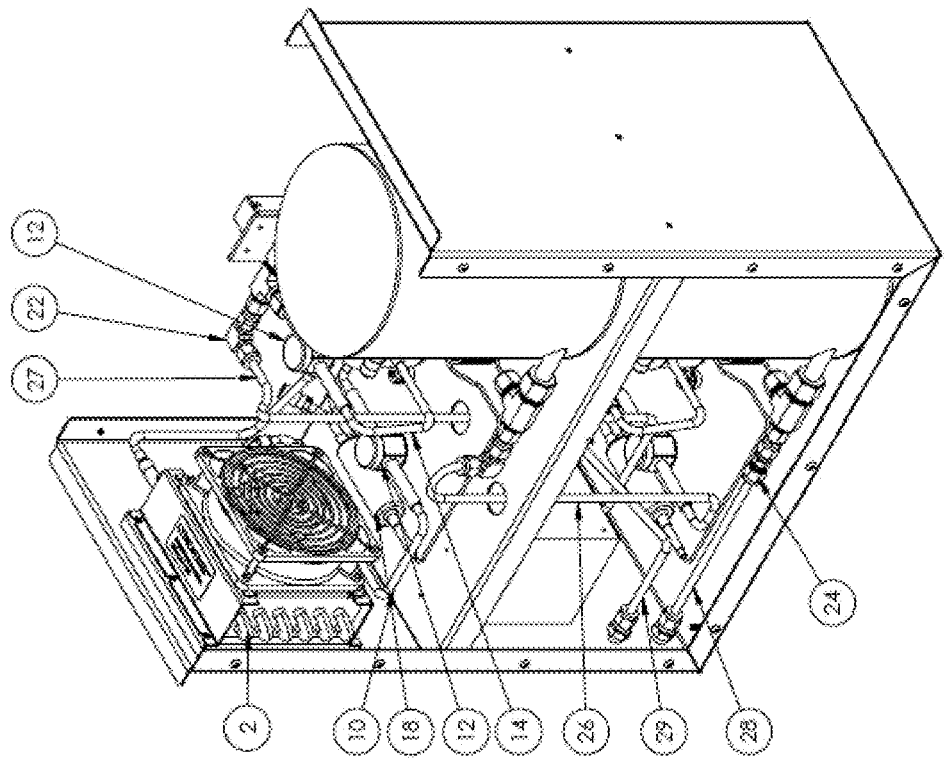

FIG. 6 illustrates test data for mass flow rate vs. temperature at 750 rpm pump speed. The data is focused around the temperature of −10° C., where pumping consistency increases and mass flow rate and pumping efficiency also begin to increase with decreasing temperatures. At an average temperature of −0.13° C., average mass flow rate was 0.158 kg/min with a standard deviation of 0.003. At an average temperature of −8.1° C., average mass flow rate was 0.173 kg/min with a standard deviation of 0.0047. At an average temperature of −16.2° C., average mass flow rate was 0.181 kg/min with a standard deviation of 0.001. At an average temperature of −23.87° C., average mass flow rate was 0.192 kg/min with a standard deviation of 0.001. At an average temperature of −31.65° C., average mass flow rate was 0.201 kg/min with a standard deviation of 0.0004. All tests were performed at a constant RPM of 750, with a target pressure of 2,000 psi and set point flow rate of 70 mL/min. The data shows a trend of increasing mass flow rate below −10° C. and decreased variation.

Example 2

Separation of Aceptophenone and Methyl Paraben 0.1 grams of Aceptophenone and 0.1 grams of Methyl Paraben were dissolved in 2 mls of Ethyl Acetate. This sample was injected into the sample loop of the SCF CO2 Flash Chromatography unit with a flow rate of 50 mls/minute of SCF CO2 and 10 mls/min of Ethyl Acetate at 1750 psi (120 Bar) and 50° C. These materials were separated through the 40 gram silica cartridge column and collected in cyclonic separators with a 99%+efficiency.

The SCF CO2 Flash unit, for the purposes of the present and following examples, was operated at 50 mls/minute SCF CO2 and 10 mls/minute up to 17.5 mls/minute of modifier co-solvent in an isocratic or gradient mode at 1750 psi (120 bar) and 50° C. The SCF CO2 Flash Chromatography unit is capable of operation up to 2500 psi (175 bar) with a SCF CO2 flow rate of 250 mls/minute and co-solvent modifier flow rate of up to 100 mls/minute with a maximum operational temperature of 100° C. The Ultra-Chiller cools the CO2 liquid coming from the supply tank from ambient temperature down to −25° C. to −30° C. which allows for efficient and accurate pumping of the SCF CO2. Once the SCO2 liquid has been pumped, it flows through a pre heater that brings the fluid from the −25° C. to −30° C. pump exit temperature up to operation temperatures of up to 100° C. The fluid streams (a supercritical fluid, e.g., supercritical CO2, and Co-Solvent modifier) flow through a static mixer that ensures the homogeneous mixing of the fluids for delivery to the column assembly. Sample introduction into the unit occurs in two modes: samples dissolved in solvent up to 5 mls in size are introduced through a sample injection loop, larger samples can be introduced through a column injection manifold (reaction mixture is evaporated onto a course silica gel that is placed in the column assembly for injection).

Figure 18:
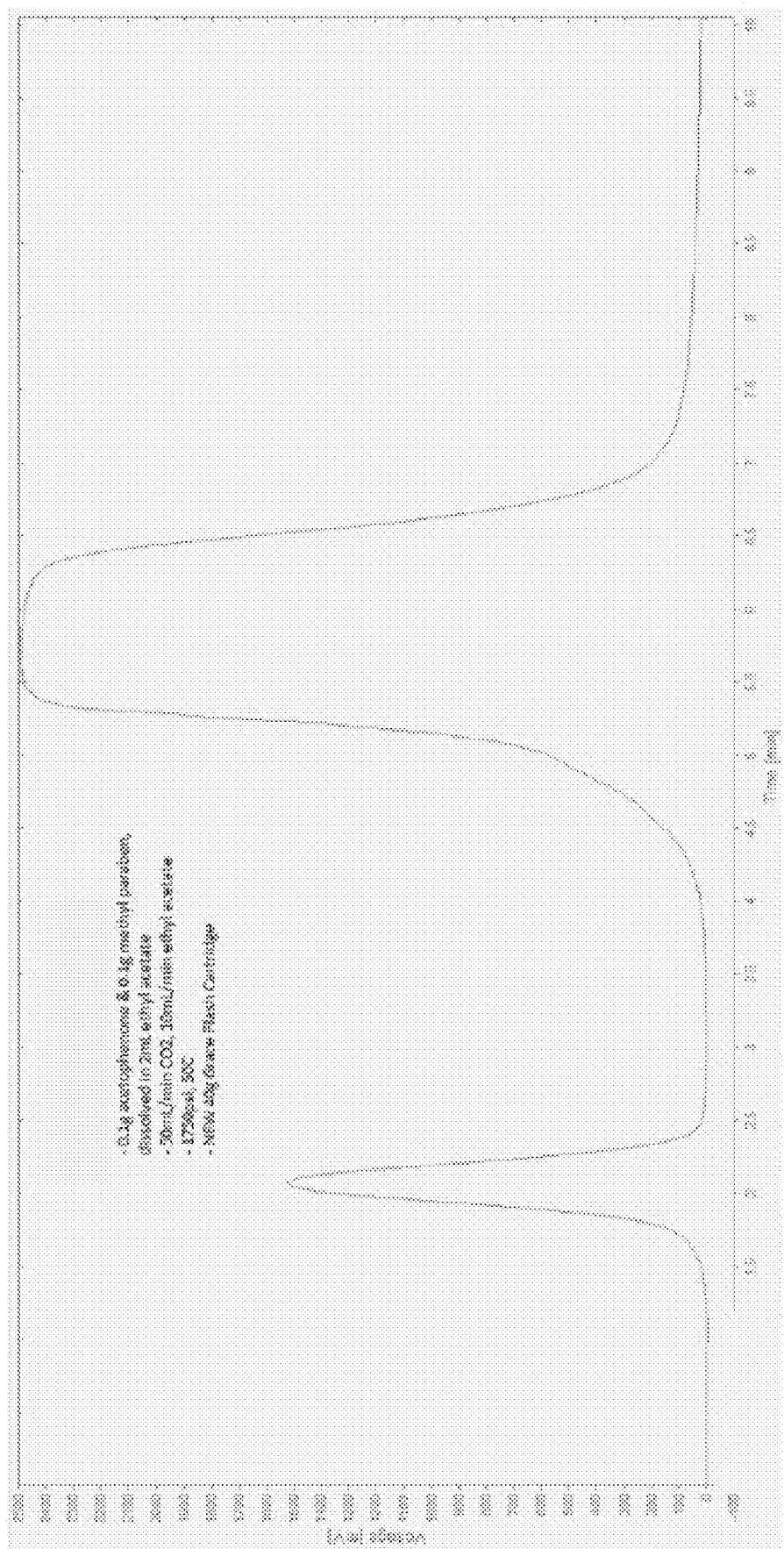
FIG. 18 illustrates a separation of aceptophenone and methyl paraben using the chromatography system described herein.

For the purposes of this work a 40 gram W. R. Grace traditional flash cartridge was used (Grace Reveleris Silica 40 micron, 40 gram, Lot #09071032, P/N 5146132, Pressure Rating 200 psi). However, the pressure equalizing vessel or Column Cartridge Containment Assembly can accommodate traditional flash cartridges from Grace (4 grams up to 330 grams in size) and flash cartridges from other flash chromatography vendors (Silicycle (silicycle.com), Biotage (biotage.com), Teledyne-ISCO (isco.com), Buchi (buchi.com), etc). The UV-Vis detector was set to 254 nm to detect the fractions coming from the separation column to then be collected in the Cyclonic Separator Assemblies. Each individual peak can be collected as a pure fraction. The results are shown in FIG. 18.

Example 3

Figure 19:
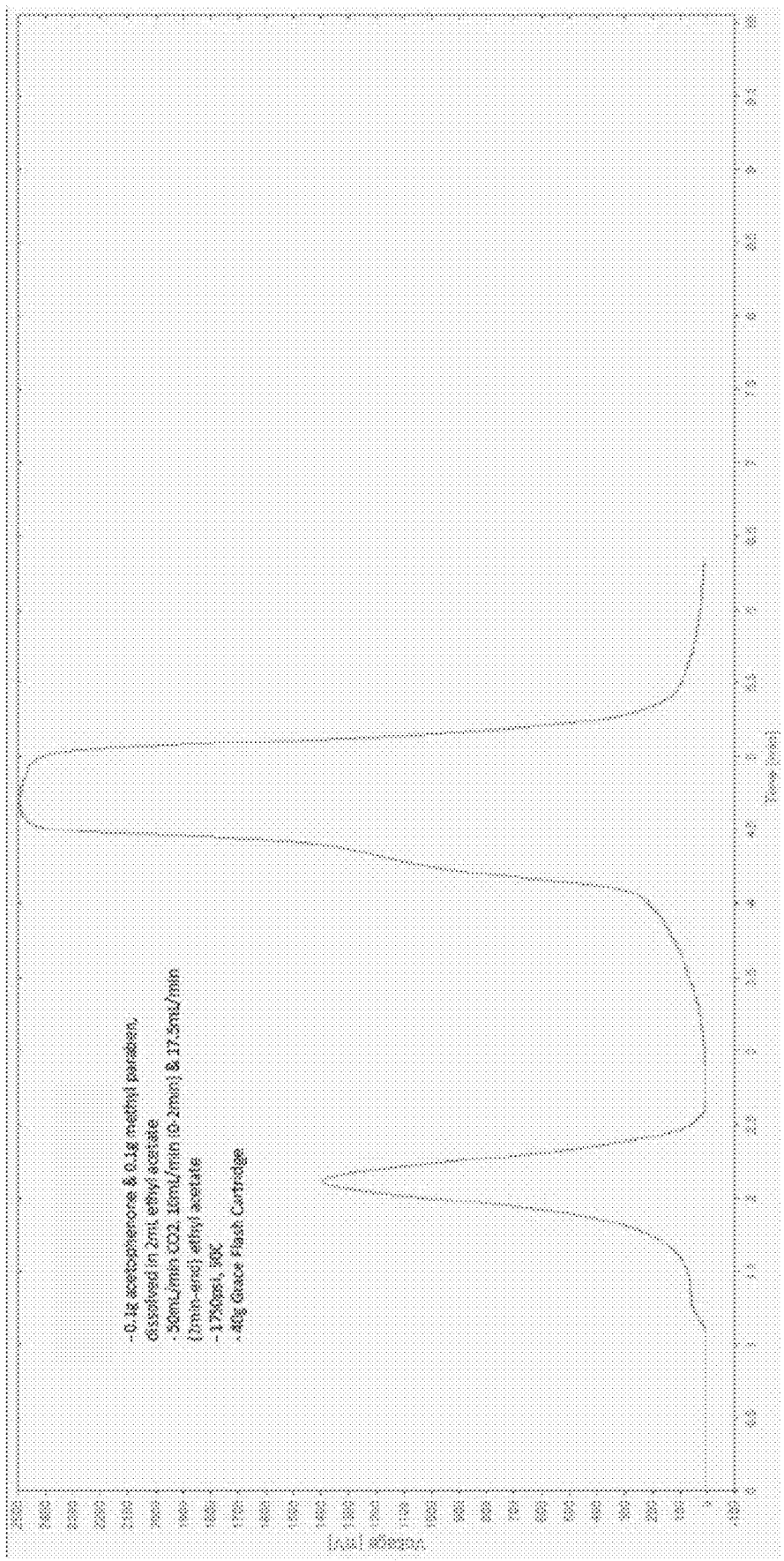
FIG. 19 illustrates a separation of aceptophenone and methyl paraben using the chromatography system described herein.

Separation of Aceptophenone and Methyl Paraben 0.1 grams of Aceptophenone and 0.1 grams of Methyl Paraben were dissolved in 2 mls of Ethyl Acetate. This sample was injected into the sample loop of the SCF CO2 Flash Chromatography unit with a flow rate of 50 mls/minute of SCF CO2 and gradient of 10 mls/min to 17.5 mls/min of Ethyl Acetate at 1750 psi (120 Bar) and 50° C. These materials were separated through the 40 gram silica cartridge column and collected in cyclonic separators with a 99%+efficiency. The results are shown in FIG. 19.

Example 4

Figure 20:
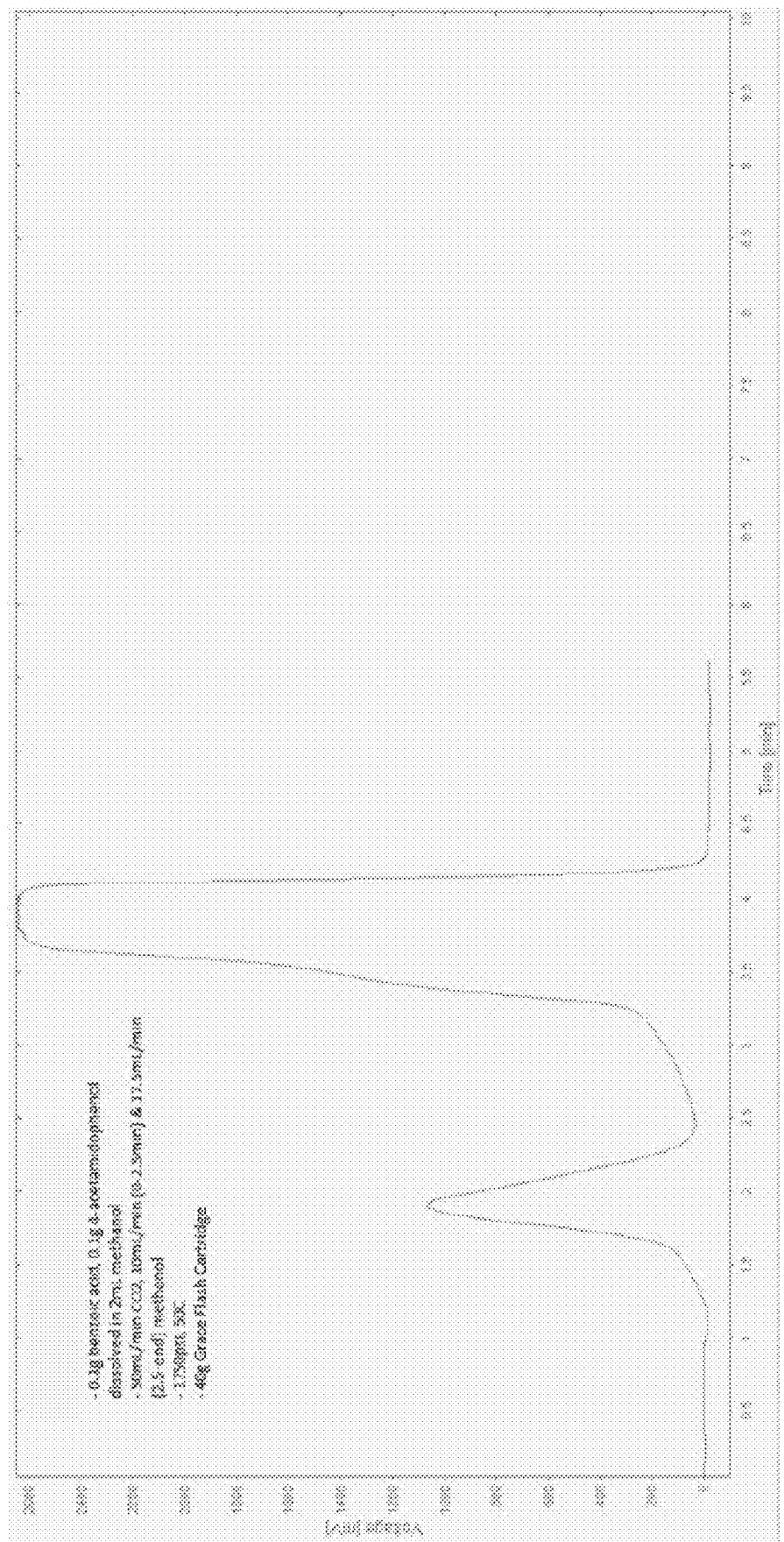
FIG. 20 illustrates a separation of benzoic acid and 4-acetamidophenol using the chromatography system described herein.

Separation of Benzoic Acid and 4-Acetamidophenol 0.1 grams of benzoic acid and 0.1 grams of 4-acetamidophenol were dissolved in 2 mls of Methanol. This sample was injected into the sample loop of the SCF CO2 Flash Chromatography unit with a flow rate of 50 mls/minute of SCF CO2 and gradient of 10 mls/min to 17.5 mls/min of Methanol at 1750 psi (120 Bar) and 50° C. These materials were separated through the 40 gram silica cartridge column and collected in cyclonic separators with a 99%+efficiency. The results are shown in FIG. 20.

Example 5

Figure 21:
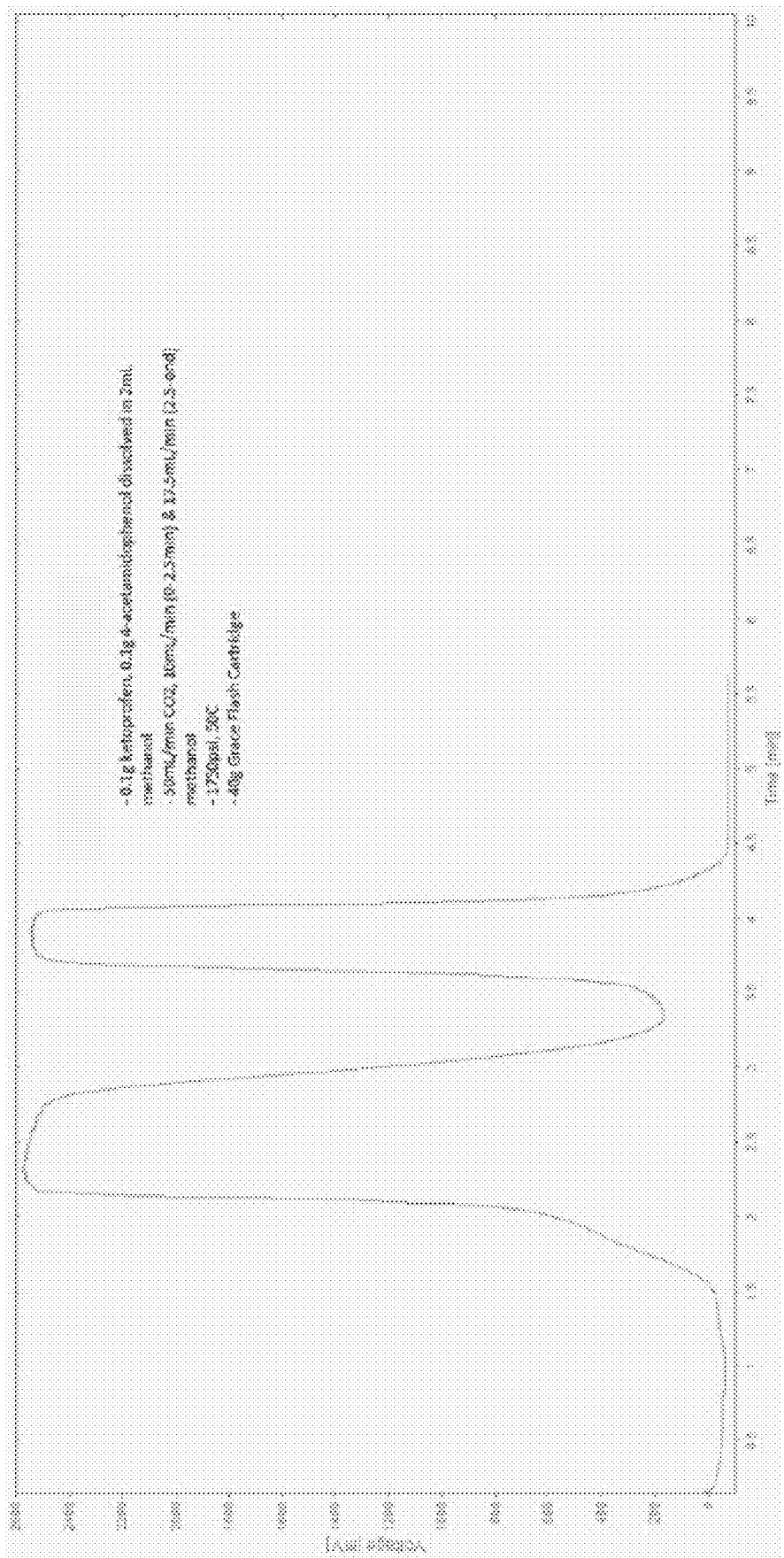
FIG. 21 illustrates a separation of ketoprofen and 4-acetamidophenol using the chromatography system described herein.

Separation of Ketoprofen and 4-Acetamidophenol 0.1 grams of ketoprofen and 0.1 grams of 4-acetamidophenol were dissolved in 2 mls of Methanol. This sample was injected into the sample loop of the SCF CO2 Flash Chromatography unit with a flow rate of 50 mls/minute of SCF CO2 and gradient of 10 mls/min to 17.5 mls/min of Methanol at 1750 psi (120 Bar) and 50° C. These materials were separated through the 40 gram silica cartridge column and collected in cyclonic separators with a 99%+efficiency. The results are shown in FIG. 21.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A pressure equalizing chromatography vessel for a supercritical fluid chromatography system, said vessel comprising:
   i) an inner chromatography column having an outer wall extending latitudinally with an outer diameter and the outer wall extending longitudinally with a length, the inner chromatography column comprising stationary phase media; and
   ii) an outer column that cylindrically surrounds the length of the inner chromatography column,
      wherein an interspace void region exists between the inner diameter of the outer column and the outer diameter of the outer wall of the inner chromatography column such that the interspace extends the length of the outer wall of the inner chromatography column and comprises a width of at least 1 mm,
      wherein the outer column withstands pressures of at least about 500 psi (about 35 bar), wherein no part of the inner chromatography column is exposed to an interior-to-exterior pressure differential greater than about 200 psi (about 14 bar);
   wherein the inner chromatography column is a pre-packed disposable plastic cartridge compatible for use in a flash chromatography system; and
   wherein there is no fluid communication between the interspace and the interior of the inner chromatography column.

2. The pressure equalizing vessel of claim 1, wherein the interspace between the inner diameter of the outer column and the outer diameter of the inner chromatography column is filled with a supercritical fluid under a pressure in the range of about 500 psi (about 35 bar) to about 20,000 psi (about 1380 bar).

3. The pressure equalizing vessel of claim 2, wherein the inner chromatography column and the outer column can be concurrently filled with supercritical fluid under a pressure of at least about 1000 psi (about 69 bar).

4. The pressure equalizing vessel of claim 3, wherein the inner chromatography column and the outer column can be concurrently filled with supercritical fluid under a pressure of at least about 5076 psi (at least about 350 bar).

5. The pressure equalizing vessel of claim 1, wherein the inner chromatography column is configured to withstand pressures no greater than about 200 psi (14 bar).

6. The pressure equalizing vessel of claim 1, wherein the pressure differential between the internal space of the inner chromatography column and the interspace is at or less than about 14 psi (about 1 bar).

7. The pressure equalizing vessel of claim 1, wherein the pressure within the interspace is higher than the pressure within the internal space of the inner chromatography column.

8. The pressure equalizing vessel of claim 1, wherein the inner chromatography column comprises an inlet end and an outlet end and the pressure at the inlet end is substantially the same as the pressure at the outlet end.

9. The pressure equalizing vessel of claim 1, wherein the inner chromatography column comprises a capacity size in the range of from about 4 grams to about 350 grams stationary phase media.

10. The pressure equalizing vessel of claim 1, wherein the inner chromatography column comprises a diameter in the range of about 0.5 inches to about 3.5 inches and a column length in the range from about 3.5 inches to about 11 inches.

11. The pressure equalizing vessel of claim 1, wherein the stationary phase media comprises an average particle size in the range of about 10 to about 100 microns.

12. The pressure equalizing vessel of claim 1, wherein the vessel comprises an inlet adaptor which fits to a female slip or luer-lock connector.

13. The pressure equalizing vessel of claim 1, wherein the vessel comprises an outlet adaptor which fits to a male slip or luer-lock connector.

14. The pressure equalizing vessel of claim 13, wherein the outlet adaptor comprises an O-ring that seals around the male slip or luer-lock connector.

15. The pressure equalizing vessel of claim 1, wherein the inner chromatography column comprises an inlet end and an outlet end, wherein neither the inlet end nor the outlet end of the inner column comprises a perforated stopper.

16. The pressure equalizing vessel of claim 1, wherein the interspace comprises a single inlet and no outlet or vent.

17. A chromatography system comprising the pressure equalizing chromatography vessel of claim 1, wherein the system is configured to be pressurized and pump a supercritical solvent through the system at a flow rate in the range of about 10 ml/min to about 300 ml/min.

18. The system of claim 17, wherein the system further pumps a co-solvent.

19. A method of performing high pressure separation and/or extraction procedures using a flash chromatography system, comprising separating sample in a supercritical fluid mobile phase in the inner chromatography column of the pressure equalizing chromatography vessel of claim 1.

* * * * *